United States Patent
Shukla et al.

(10) Patent No.: US 10,114,851 B2
(45) Date of Patent: Oct. 30, 2018

(54) SYSTEMS AND METHODS FOR VERIFIABLE, PRIVATE, AND SECURE OMIC ANALYSIS

(71) Applicants: Sachet Ashok Shukla, Newton, MA (US); Madhukar Anand, Fremont, CA (US); Jahnavi Chandra Prasad, Wilmington, DE (US)

(72) Inventors: Sachet Ashok Shukla, Newton, MA (US); Madhukar Anand, Fremont, CA (US); Jahnavi Chandra Prasad, Wilmington, DE (US)

( * ) Notice: Subject to any disclaimer, the term of this patent is extended or adjusted under 35 U.S.C. 154(b) by 798 days.

(21) Appl. No.: 14/605,928

(22) Filed: Jan. 26, 2015

(65) Prior Publication Data

US 2015/0213079 A1    Jul. 30, 2015

Related U.S. Application Data

(60) Provisional application No. 61/931,259, filed on Jan. 24, 2014.

(51) Int. Cl.
*H04L 9/00* (2006.01)
*H04L 9/32* (2006.01)
(Continued)

(52) U.S. Cl.
CPC ........ *G06F 17/30371* (2013.01); *G06F 19/28* (2013.01); *G06F 21/6263* (2013.01);
(Continued)

(58) Field of Classification Search
None
See application file for complete search history.

(56) References Cited

U.S. PATENT DOCUMENTS 7,158,892 B2   1/2007  Robson et al.
7,702,104 B2   4/2010  Batra et al.
(Continued)

FOREIGN PATENT DOCUMENTS

WO   WO 2008/135951 A1   11/2008
WO   WO 2012/158640 A1   11/2012
(Continued)

OTHER PUBLICATIONS

Vladimir Kolesnikov, "Gate Evaluation Secret Sharing and Secure One-Round Two-Party Computation", 2005, International Association for Cryptologic Research, B. Roy (Ed.): ASIACRYPT 2005, LNCS 3788, pp. 136-155.*

(Continued)

*Primary Examiner* — Neveen Abel Jalil
*Assistant Examiner* — Katriel Y Chiu
(74) *Attorney, Agent, or Firm* — Brad Bertoglio

(57) ABSTRACT

Systems and methods for verifiable, private and secure omic analysis are provided. Secure multiparty computation techniques can be utilized to enable two parties to perform an omic transaction, such as determining genetic compatibility with one another, by jointly computing a result without either party disclosing their genetic information to the other. Privacy-preserving techniques to ensure authenticity of each party's omic data and metadata are also provided. Personalized matching scores can be computed, in which each party's score is weighted to reflect user preferences associated with the matching analysis.

17 Claims, 15 Drawing Sheets

(51) Int. Cl.
*G06F 17/30* (2006.01)
*G06F 21/62* (2013.01)
*H04L 29/06* (2006.01)
*G06F 19/28* (2011.01)

(52) U.S. Cl.
CPC ............ *H04L 9/008* (2013.01); *H04L 9/3231* (2013.01); *H04L 63/10* (2013.01); *H04L 2209/46* (2013.01)

(56) References Cited

U.S. PATENT DOCUMENTS

| | | | |
|---|---|---|---|
| 8,452,619 | B2 | 5/2013 | Kenedy et al. |
| 8,600,683 | B2 | 12/2013 | George |
| 8,620,594 | B2 | 12/2013 | Silver |
| 8,630,422 | B2 | 1/2014 | Gentry |
| 8,731,956 | B2 | 5/2014 | Bejjani et al. |
| 8,806,200 | B2 | 8/2014 | Baskaran |
| 8,825,555 | B2 | 9/2014 | Gross et al. |
| 2005/0074795 | A1 | 4/2005 | Hoffman et al. |
| 2006/0080137 | A1 | 4/2006 | Chambers et al. |
| 2007/0166728 | A1* | 7/2007 | Abramson .............. G06F 19/26 435/6.11 |
| 2009/0177487 | A1 | 7/2009 | Eerkes |
| 2009/0182579 | A1 | 7/2009 | Liu |
| 2009/0240441 | A1 | 9/2009 | Lapidus |
| 2010/0022406 | A1 | 1/2010 | Srinivasan et al. |
| 2010/0191975 | A1 | 7/2010 | Chase et al. |
| 2010/0256988 | A1 | 10/2010 | Barnhill et al. |
| 2010/0299531 | A1 | 11/2010 | Webster et al. |
| 2011/0110525 | A1* | 5/2011 | Gentry .................. H04L 9/0822 380/285 |
| 2011/0124515 | A1 | 5/2011 | Silver |
| 2012/0143512 | A1 | 6/2012 | Reese et al. |
| 2012/0260346 | A1 | 10/2012 | Carey et al. |
| 2012/0264115 | A1* | 10/2012 | Rava ....................... G06F 19/22 435/6.1 |
| 2013/0006867 | A1 | 1/2013 | Dove et al. |
| 2013/0096943 | A1 | 4/2013 | Carey et al. |
| 2013/0254255 | A1 | 9/2013 | Nilsson et al. |
| 2013/0339958 | A1 | 12/2013 | Droste et al. |
| 2014/0012843 | A1 | 1/2014 | Soon-Shiong |
| 2014/0075183 | A1* | 3/2014 | Wang ...................... G06F 19/22 713/150 |
| 2014/0089009 | A1 | 3/2014 | Van Criekinge et al. |
| 2014/0121990 | A1* | 5/2014 | Baldi ....................... G06F 19/28 702/20 |
| 2015/0007258 | A1* | 1/2015 | Patey ........................ H04L 9/00 726/1 |
| 2015/0154646 | A1* | 6/2015 | Mishra ................... G06Q 50/24 705/3 |

FOREIGN PATENT DOCUMENTS

| | | |
|---|---|---|
| WO | WO 2013/067542 A1 | 5/2013 |
| WO | WO 2014/040964 A1 | 3/2014 |
| WO | WO 2014/134615 A1 | 9/2014 |

OTHER PUBLICATIONS

Jha et al, "Towards Practical Privacy for Genomic Computation" 2008 IEEE Symposium on Security and Privacy (2008).

Snyder, "Yao's Garbled Circuits: Recent Directions and Implementations".

Troncoso-Pastoriza et al., "Privacy Preserving Error Resilient DNA Searching through Oblivious Automata", CCS '07 (Oct. 29-Nov. 2, 2007).

Atallah et al., "Secure and Private Sequence Comparisons" WPES '03 (Oct. 30, 2003).

Atallah et al. "Secure Outsourcing of Sequence Comparisons" CERIAS Tech Report 2005-126 (2005).

Blanton et al, "Secure Outsourcing of DNA Searching via Finite Automata" Dept Computer Sci and Engineering, Univ of Notre Dame.

Franz et al., "Towards Secure Bioinformatics Services" FC 2011, LNCS 7035 (2012).

* cited by examiner

SYSTEMS AND METHODS FOR VERIFIABLE, PRIVATE, AND SECURE OMIC ANALYSIS

TECHNICAL FIELD

The disclosure relates in general to data processing, and in particular to systems, and methods for privacy-preserving analysis of omic data.

BACKGROUND

Multivariate profiling on an individual's biological makeup for medical, prognostic and personal use is becoming commonplace. These omic techniques encompass various modalities such as genomic, proteomic, metabolomic, epigenomic, and metagenomic profiling. In particular, genetic sequencing and profiling technology has advanced rapidly in recent years. The cost of genome sequencing is plummeting, while the availability of genomic sequencing technology is becoming more prevalent around the world. Simultaneously, we are rapidly improving our ability to draw meaningful personal health information from genomic data. We are quickly moving towards an environment in which individuals will be able to affordably have their whole genome sequenced and utilized regularly for personalized health insight and medical treatment. This may also be accompanied by a rapid proliferation of omic transactions between two or more participating entities in scenarios such as two individuals wanting to compare their omic information to determine their compatibility in terms of health of future progeny.

However, personal genome sequencing gives rise to significant challenges relating to privacy, information authentication and information verification. Genetic sequence data can reveal highly sensitive information about an individual, including the presence or propensity to develop genetic diseases and conditions, and even behavioral predispositions. Malicious use of genetic data could lead to privacy violation, genetic discrimination, and other harmful results. Therefore, individuals may desire to maintain their genetic information private from other people against whom they would like to test for potential compatibility, such as propensity for genetic disease in potential offspring, as well as from doctors and service providers who may require access to a limited portion of genetic information for limited purposes. Accordingly, to unlock the full potential benefits of genetic sequencing and analysis, it may be important to provide mechanisms for preserving the privacy of genomic sequence data.

One particularly valuable use of genomic computation is for evaluating the compatibility of individuals for purposes of having children, and specifically for identifying potential risks of genetic disease or other attributes in the potential offspring. Individuals being tested for compatibility may desire to learn specific information regarding their potential offspring, while avoiding or minimizing any potential disclosure of their own genetic information. Solutions to this issue have been proposed. One approach is for individuals to each provide their genomic data to a trusted third party for analysis, with the primary parties receiving only the results of the testing. However, in such a scenario, a participant's genomic privacy could be readily violated as a result of malicious action on or by the third party testing facility, such as a hacking attack, employee misconduct or organizational misuse. Furthermore, with such testing facilities potentially acting as centralized repositories for highly sensitive genetic information, they may be particularly susceptible likely to be targeted for attack.

Another approach to preserve privacy in genomic transactions is to utilize combinations of data encryption and computational techniques in order to enable calculations on genomic data, without revealing the entirety of that genomic data to any one party. Such techniques are described in, e.g., PCT Patent Publication Nos. WO 2014/040964 A1 and WO 2013/067542 A1 and WO 2008/135951 A1. One such technique that has been applied to genomic data is Secure Multiparty Computation (hereinafter, "SMC"). SMC techniques, such as Yao's Garbled Circuits technique, enable two parties to jointly compute a function while keeping their inputs private. SMC has been utilized to enable two individuals to test their genetic compatibility without disclosing their gene sequence data to one another.

Another approach to computational privacy is homomorphic encryption. In theory, homomorphic encryption techniques enable individuals to perform computations on encrypted data, without decrypting the data, thereby yielding a computationally sound result of a calculation without disclosing the input data.

While computational privacy techniques such as SMC and homomorphic encryption may protect against malicious breach of genetic privacy, they are also highly computationally intensive. As such, for certain applications they may require a burdensome or even impractical amount of time or computational resources. Also, traditional SMC and homomorphic encryption approaches may not address other characteristics that may be desirable in a platform for genomic computation. For example, in a computation platform testing for genetic compatibility between potential mates, it may be important to provide for verification of data integrity to ensure that the other party's genomic data has not been intentionally altered or unintentionally corrupted. Users or operators of such a platform may also desire to provide for data authentication, to verify that provided genomic data actually belongs to the intended individual. The success and desirability of certain genomic computation platforms may also require a convenient mechanism by which users can securely interact with the platform. Some of these and other factors may be addressed by certain of the embodiments described hereinbelow.

SUMMARY

The present disclosure describes systems and methods for privacy-preserving computation on genomic information. In accordance with one embodiment, an omic compatibility matching service is hosted on a first computing device, communicating with users having a second computing device and a third computing device, the computing devices communicating via a digital communications network to execute an omic matching transaction. The first computing device has one or more processors and memory storing instructions which, when executed by the processors, cause the first computing device to perform a method. The method includes generating, by a first computing device, a calculation descriptor for testing the compatibility of two sets of omic data; generating, by the first computing device, verification data; generating, by the first computing device, a verification calculation descriptor; providing, by the first computing device, the calculation descriptor and the verification calculation descriptor to a second computing device; providing, by the first computing device, the calculation descriptor to a third computing device; calculating, by the first computing device and the second computing device, a verification output using the verification calculation descriptor and a first set of omic data maintained by the second computing device; determining, by the first computing device, that the verification output matches the verification data; and directing, by the first computing device, the calculation of a compatibility score, by the second and third computing devices, using a secure function evaluation based on the calculation descriptor, the first set of omic data, and a second set of omic data maintained by the third computing device.

In accordance with another embodiment, a method for omic compatibility matching comprises: obtaining, by a first computing device, a calculation descriptor for testing the compatibility of two sets of omic data; determining, by the first computing device, at least one first input to the calculation descriptor, using a first set of omic data accessible to the first computing device; generating, by the first computing device, at least one secure share, using the at least one first input; receiving, by the first computing device, from a second computing device, an indication that at least one second input generated by a third computing device using a second set of omic data is trustworthy; transmitting, by the first computing device, the at least one secure share to the third computing device by means of an oblivious transfer using the at least one secure share and the at least one second input; and receiving, by the first computing device, at least one output generated using the at least one secure share, the at least one second input, and the calculation descriptor.

The step of obtaining may also comprise receiving a calculation descriptor from the second device. The step of obtaining can further comprise obtaining, by the first computing device, a calculation descriptor comprising a boolean circuit comprising a set of logically interrelated gates. The method may further include: determining, by the first computing device, a subset of the first set of omic data, such that comparing the subset of the first set of omic data and a corresponding subset of the second set of omic data reproduce the at least one output; providing, by the first computing device, the subset of the first set of omic data to the second computing device; and receiving, by the first computing device and from the second computing device, a biological description regarding the at least one output, using the subset of the first set of omic data and the subset of the second omic data. The step of determining can further include: dividing the first set of omic data to obtain the subset of the first set of omic data; obtaining, by the first computing device, an additional calculation descriptor for comparing the subset of the first set of omic data with the analogous subset of the second set of omic data; determining, by the first computing device, at least one additional input to the calculation descriptor, using the subset of the first set of omic data; generating, by the first computing device, at least one additional secure share, using the at least one additional input; transmitting, by the first computing device, the at least one additional secure share to the third computing device by means of an oblivious transfer using the at least one additional secure share and an additional second input from the third computing device; receiving, by the first computing device, at least one additional output generated using the at least one secure share, the at least one second input, and the calculation descriptor; comparing, by the first computing device, the at least one additional output to the at least one output; and determining, by the first computing device, that the at least one additional output is equal to the at least one output.

In accordance with another embodiment, a method for omic compatibility matching comprises: obtaining, by a first computing device, a calculation descriptor for testing the compatibility of two sets of omic data; determining, by the first computing device, at least one first input to the calculation descriptor, using a first set of omic data accessible to the first computing device; committing, by the first computing device, to the at least one first input; obtaining, by the first computing device, a verification calculation descriptor; generating, by the first computing device, a secure verification share using the at least one first input; transmitting, by the first computing device, to a second computing device, the secure verification share, by means of an oblivious transfer using the at least one secure verification share and an input created by the second computing device; receiving, by the first computing device, at least one secure share obtained from a second set of omic data, from a third computing device by means of an oblivious transfer using the at least one secure share and the at least one first input; and calculating, by the first computing device, at least one output using the at least one secure share, the at least one first input, and the calculation descriptor.

In some embodiments, the calculation descriptor is a boolean circuit comprising a set of logically interrelated gates, and having a first set of input wires corresponding to the first set of omic data, and a second set of input wires corresponding to the second set of omic data. The step of calculating can further comprise calculating using a Gate Evaluation Secret Sharing scheme.

Systems and methods are also provided for determining personalized compatibility scores for each user. In one embodiment, a method for evaluating omic compatibility amongst a plurality of sets of omic data, at least one of which is associated with a user, includes selecting a set of comparison attributes from amongst a plurality of omic attributes for comparing the sets of omic data; obtaining user preferences associated with the user; determining user-specific weighting factors for the attributes based on the user preferences; computing of a numerical subscore for each attribute by comparing the sets of omic data based upon the selected set of comparison attributes; applying the user-specific weighting factors to the numerical subscores for each attribute to generate custom-weighted subscores for each user; and calculating a personalized matching score by combining the custom-weighted subscores for each user. The personalized matching score may be a reproductive compatibility score indicative of reproductive compatibility between two users. The plurality of sets of omic data may include an omic data set of associated with a biological organism, and one or more data sets associated with a probability of developing one or more illnesses, such that the personalized matching score is a disease risk assessment score evaluating risk of the biological organism developing the one or more illnesses. At least one of the plurality of sets of omic data may be associated with a potential organ donee, and at least one of the plurality of sets of omic data is associated with an organ donor; and in which the matching score is an organ donation compatibility score. In other applications, the plurality of sets of omic data may include a first set of omic data associated with a first biological organism, and a second set of omic data associated with a second biological organism; such that the matching score is a relatedness score, determining relatedness between the first and second biological organisms. In another application, the comparison attributes include one or more phenotypic attributes; and the user preferences comprise preferences for traits associated with said phenotypic attributes.

Various other objects, features, aspects, and advantages of the present invention and embodiments will become more apparent from the following detailed description of preferred embodiments, along with the accompanying drawings in which like numerals represent like components.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

Figure 1A:
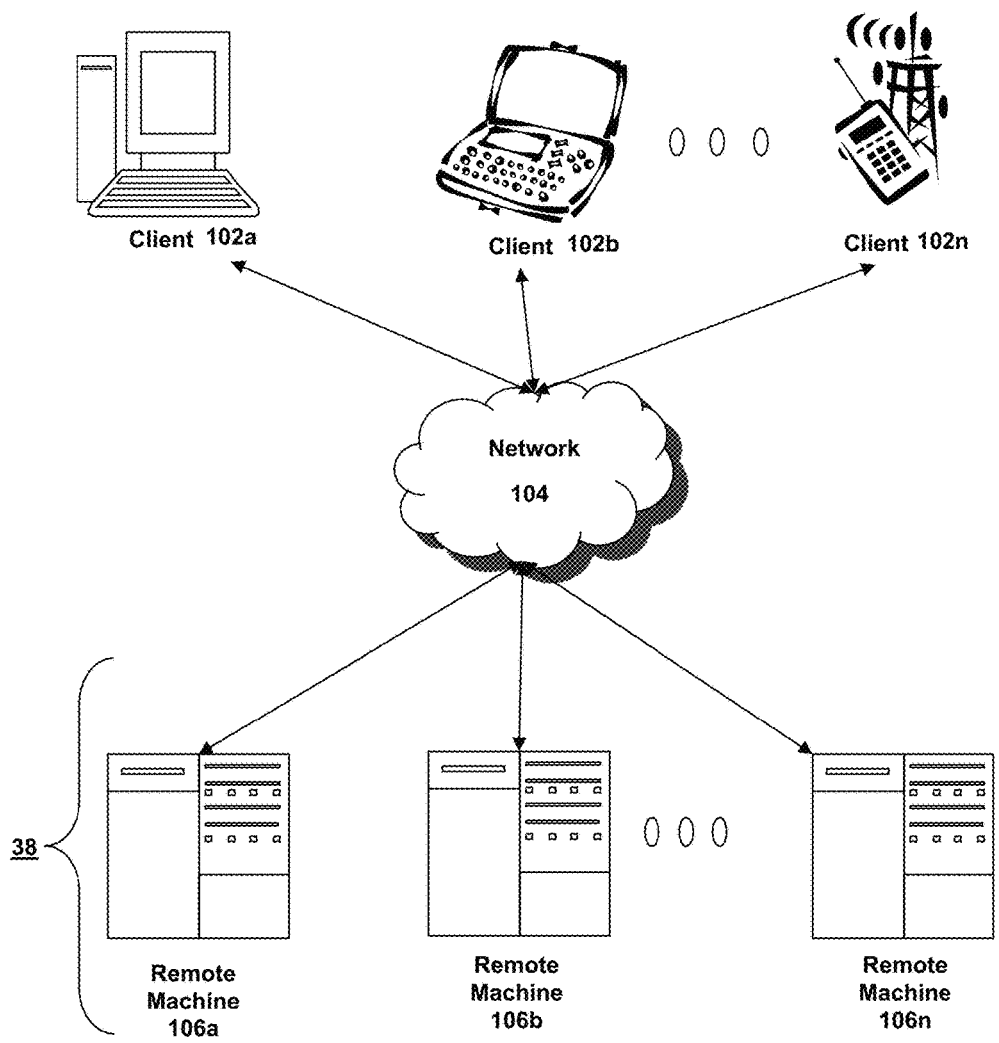
FIG. 1A is a block diagram depicting an embodiment of a computer network environment useful in connection with the methods and systems described herein.

While this invention is susceptible to embodiment in many different forms, there are shown in the drawings and will be described in detail herein several specific embodiments, with the understanding that the present disclosure is to be considered as an exemplification of the principles of the invention to enable any person skilled in the art to make and use the invention, and is not intended to limit the invention to the embodiments illustrated.

In some embodiments, the methods and systems described herein relate to privacy-preserving, omic-matching functionality using secure multiparty computation. Before describing such methods and systems in detail, however, a description is provided of a network in which such methods and systems may be implemented.

Network and Computing Environments

Referring now to FIG. 1A, an embodiment of a network environment is depicted. In brief overview, the network environment comprises one or more clients $102a$-$102n$ (also generally referred to as local machine(s) 102, client(s) 102, client node(s) 102, client machine(s) 102, client computer(s) 102, client device(s) 102, computing device(s) 102, endpoint(s) 102, or endpoint node(s) 102) in communication with one or more remote machines $106a$-$106n$ (also generally referred to as server(s) 106 or computing device(s) 106) via one or more networks 104.

Although FIG. 1A shows a network 104 between the clients 102 and the remote machines 106, the clients 102 and the remote machines 106 may be on the same network 104. The network 104 can be a local-area network (LAN), such as a company Intranet, a metropolitan area network (MAN), or a wide area network (WAN), such as the Internet or the World Wide Web. In some embodiments, network 104 may be made up from multiple, preferably interconnected, networks between the clients 102 and the remote machines 106. For example, network 104 may include multiple private networks, multiple public networks, or combinations of public and private networks.

The network 104 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol or protocols used to communicate among mobile devices, including AMPS, TDMA, CDMA, GSM, GPRS, or UMTS. In some embodiments, different types of data may be transmitted via different protocols. In other embodiments, the same types of data may be transmitted via different protocols.

A client 102 and a remote machine 106 (referred to generally as computing devices 100) can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client 102 may execute, operate or otherwise provide an application, which can be any type and/or form of software, program, or executable instructions, including, without limitation, any type and/or form of web browser, web-based client, client-server application, an ActiveX control, or a Java applet, or any other type and/or form of executable instructions capable of executing on client 102.

In one embodiment, a computing device 106 provides functionality of a web server. In some embodiments, a web server 106 comprises an open-source web server, such as the APACHE servers maintained by the Apache Software Foundation of Delaware. In other embodiments, the web server executes proprietary software, such as the Internet Information Services products provided by Microsoft Corporation of Redmond, Wash.; the Oracle iPlanet web server products provided by Oracle Corporation of Redwood Shores, Calif.; or the BEA WEBLOGIC products provided by BEA Systems of Santa Clara, Calif.

In some embodiments, the system may include multiple, logically-grouped remote machines 106. In one of these embodiments, the logical group of remote machines may be referred to as a server farm 38. In another of these embodiments, the server farm 38 may be administered as a single entity.

Figure 1B:
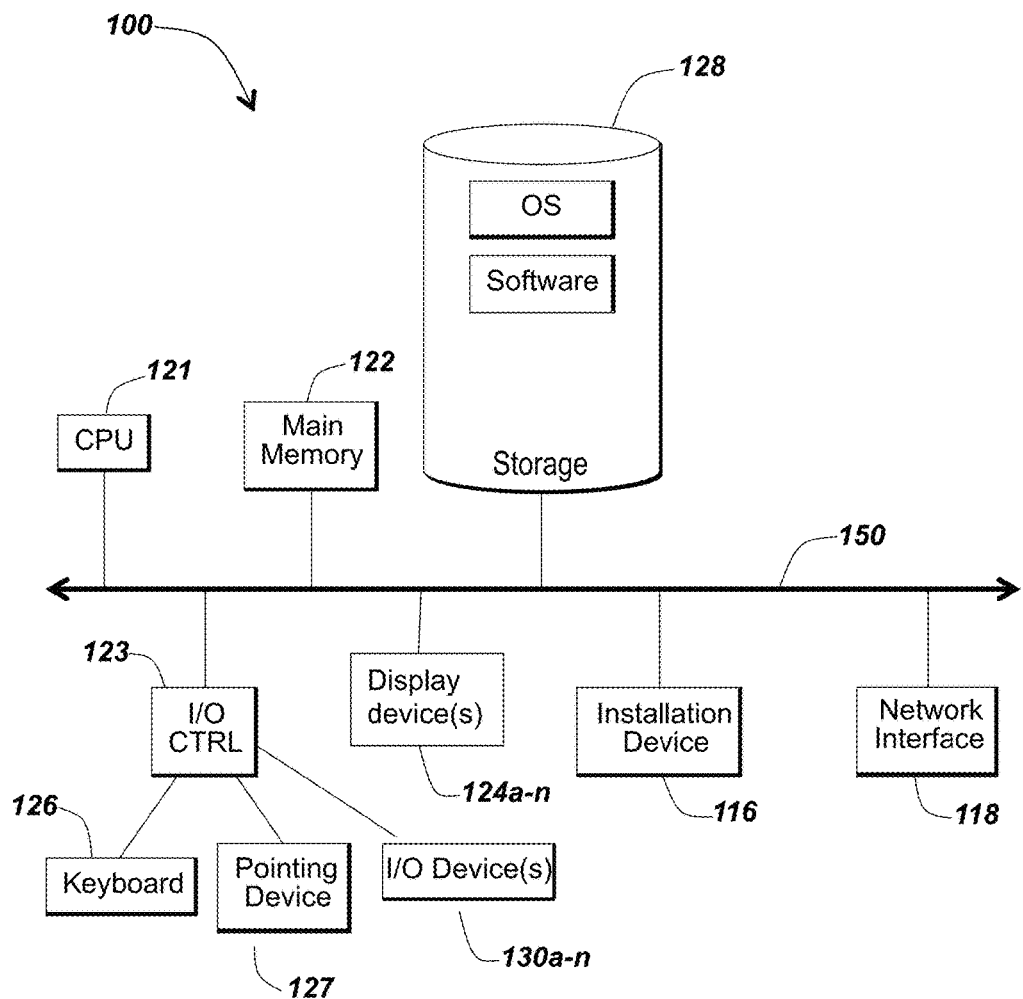
FIG. 1B is a block diagram depicting an embodiment of a computing device useful in connection with the methods and systems described herein.
Figure 1C:
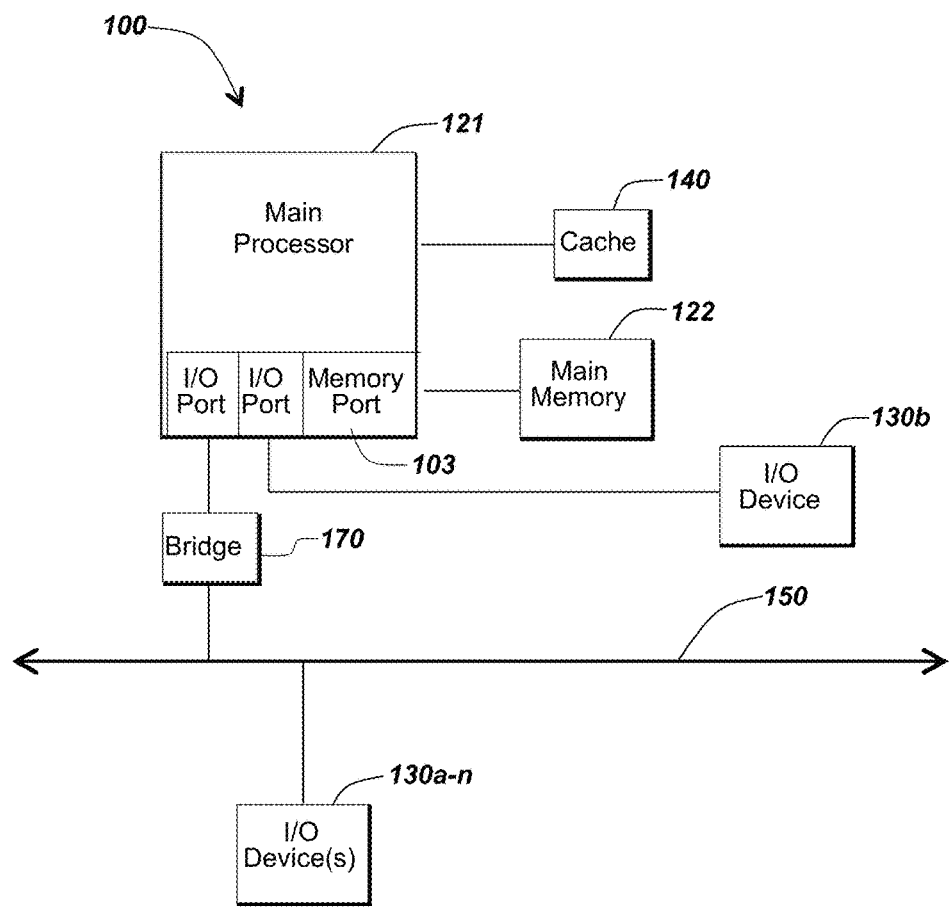
FIG. 1C is a block diagraph depicting an embodiment of a computing device useful in connection with the methods and systems described herein.

FIGS. 1B and 1C depict block diagrams of a computing device 100 useful for practicing an embodiment of the client 102 or a remote machine 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-n, a keyboard 126, a pointing device 127, such as a mouse, and one or more other I/O devices 130a-n. The storage device 128 may include, without limitation, an operating system and software. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit such as: those manufactured by Intel Corporation of Mountain View, Calif.; those manufactured by Motorola Corporation of Schaumburg, Ill.; those manufactured by Transmeta Corporation of Santa Clara, Calif.; those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 121. The main memory 122 may be based on any available memory chips capable of operating as described herein. In the embodiment shown in FIG. 1B, the processor 121 communicates with main memory 122 via a system bus 150. FIG. 1C depicts an embodiment of a computing device 100 in which the processor communicates directly with main memory 122 via a memory port 103. FIG. 1C also depicts an embodiment in which the main processor 121 communicates directly with cache memory 140 via a secondary bus, sometimes referred to as a backside bus. In other embodiments, the main processor 121 communicates with cache memory 140 using the system bus 150.

In the embodiment shown in FIG. 1B, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 also communicates directly with an I/O device 130b via, for example, HYPERTRANSPORT, RAPIDIO, or INFINIBAND communications technology.

A wide variety of I/O devices 130a-130n may be present in the computing device 100. Input devices include keyboards, mice, trackpads, trackballs, microphones, scanners, cameras, and drawing tablets. Output devices include video displays, speakers, inkjet printers, laser printers, and dye-sublimation printers. The I/O devices may be controlled by an I/O controller 123 as shown in FIG. 1B. Furthermore, an I/O device may also provide storage and/or an installation medium 116 for the computing device 100. In some embodiments, the computing device 100 may provide USB connections (not shown) to receive handheld USB storage devices such as the USB Flash Drive line of devices manufactured by Twintech Industry, Inc. of Los Alamitos, Calif.

Referring still to FIG. 1B, the computing device 100 may support any suitable installation device 116, such as a floppy disk drive for receiving floppy disks such as 3.5-inch disks, 5.25-inch disks or ZIP disks, a CD-ROM drive, a CD-R/RW drive, a DVD-ROM drive, tape drives of various formats, USB device, hard-drive or any other device suitable for installing software and programs. The computing device 100 may further comprise a storage device, such as one or more hard disk drives or redundant arrays of independent disks, for storing an operating system and other software.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, CDMA, GSM, WiMax, and direct asynchronous connections). In one embodiment, the computing device 100 communicates with other computing devices 100' via any type and/or form of gateway or tunneling protocol such as Secure Socket Layer (SSL) or Transport Layer Security (TLS). The network interface 118 may comprise a built-in network adapter, network interface card, PCMCIA network card, card bus network adapter, wireless network adapter, USB network adapter, modem, or any other device suitable for interfacing the computing device 100 to any type of network capable of communication and performing the operations described herein.

In some embodiments, the computing device 100 may comprise or be connected to multiple display devices 124a-124n, of which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS CE, WINDOWS XP, WINDOWS 7, and WINDOWS VISTA, all of which are manufactured by Microsoft Corporation of Redmond, Wash.; MAC OS manufactured by Apple Inc. of Cupertino, Calif.; OS/2 manufactured by International Business Machines of Armonk, N.Y.; and Linux, a freely-available operating system distributed by Caldera Corp. of Salt Lake City, Utah, or any type and/or form of a Unix operating system, among others.

The computing device 100 can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some embodiments, the computing device 100 may have different processors, operating systems, and input devices consistent with the device. In other embodiments the computing device 100 is a mobile device, such as a JAVA-enabled cellular telephone or personal digital assistant (PDA). The computing device 100 may be a mobile device such as those manufactured, by way of example and without limitation, by Motorola Corp. of Schaumburg, Ill., USA; Kyocera of Kyoto, Japan; Samsung Electronics Co., Ltd. of Seoul, Korea; Nokia of Finland; Hewlett-Packard Development Company, L.P. and/or Palm, Inc. of Sunnyvale, Calif., USA; Sony Ericsson Mobile Communications AB of Lund, Sweden; or Research In Motion Limited, of Waterloo, Ontario, Canada. In yet other embodiments, the computing device 100 is a smart phone, Pocket PC, Pocket PC Phone, or other portable mobile device supporting Microsoft Windows Mobile Software.

In some embodiments, the computing device 100 is a digital audio player. In one of these embodiments, the computing device 100 is a digital audio player such as the Apple IPOD, IPOD Touch, IPOD NANO, and IPOD SHUFFLE lines of devices, manufactured by Apple Inc. of Cupertino, Calif. In another of these embodiments, the digital audio player may function as both a portable media player and as a mass storage device. In other embodiments, the computing device 100 is a digital audio player such as those manufactured by, for example, and without limitation, Samsung Electronics America of Ridgefield Park, N.J.; Motorola Inc. of Schaumburg, Ill.; or Creative Technologies Ltd. of Singapore. In yet other embodiments, the computing device 100 is a portable media player or digital audio player supporting file formats including, but not limited to, MP3, WAV, M4A/AAC, WMA Protected AAC, AEFF, Audible audiobook, Apple Lossless audio file formats, and .mov, .m4v, and .mp4 MPEG-4 (H.264/MPEG-4 AVC) video file formats.

In some embodiments, the computing device 100 comprises a combination of devices, such as a mobile phone combined with a digital audio player or portable media player. In one of these embodiments, the computing device 100 is a device in the Motorola line of combination digital audio players and mobile phones. In another of these embodiments, the computing device 100 is a device in the iPhone smartphone line of devices manufactured by Apple Inc. of Cupertino, Calif. In still another of these embodiments, the computing device 100 is a device executing the Android open source mobile phone platform distributed by the Open Handset Alliance; for example, the device 100 may be a device such as those provided by Samsung Electronics of Seoul, Korea, or HTC Headquarters of Taiwan, R.O.C. In other embodiments, the computing device 100 is a tablet device such as, for example and without limitation, the iPad line of devices manufactured by Apple Inc.; the PlayBook manufactured by Research in Motion; the Cruz line of devices manufactured by Velocity Micro, Inc. of Richmond, Va.; the Folio and Thrive line of devices manufactured by Toshiba America Information Systems, Inc. of Irvine, Calif.; the Galaxy line of devices manufactured by Samsung; the HP Slate line of devices manufactured by Hewlett-Packard; and the Streak line of devices manufactured by Dell, Inc. of Round Rock, Tex.

Systems for Privacy-Preserving Omic Computation

Embodiments of the disclosed systems and methods can be utilized for a number of different genomic (and more generally, omic) analyses, while preserving participant privacy, verifying data integrity and authenticating the data provenance. For example, embodiments can enable two people to determine their reproductive compatibility using their omic profiles, secure in the knowledge that each person is using genuine data and that neither person is sacrificing data privacy in the process. Other embodiments permit a person seeking an organ donation to assess the compatibility of donated tissue without revealing anything about the donee's omic data in the process. The use of encrypted verification, authentication, and secure multiparty computation together in an integrated system allows users to make any conceivable calculation using their omic data in a completely secure and verifiable way. In some embodiments, an authentication server using the disclosed implementations can at once guarantee that both parties to the calculation are using genuine and un-tampered-with omic data, and that the authentication server itself cannot intentionally or unintentionally violate the privacy of either party.

Figure 2A:
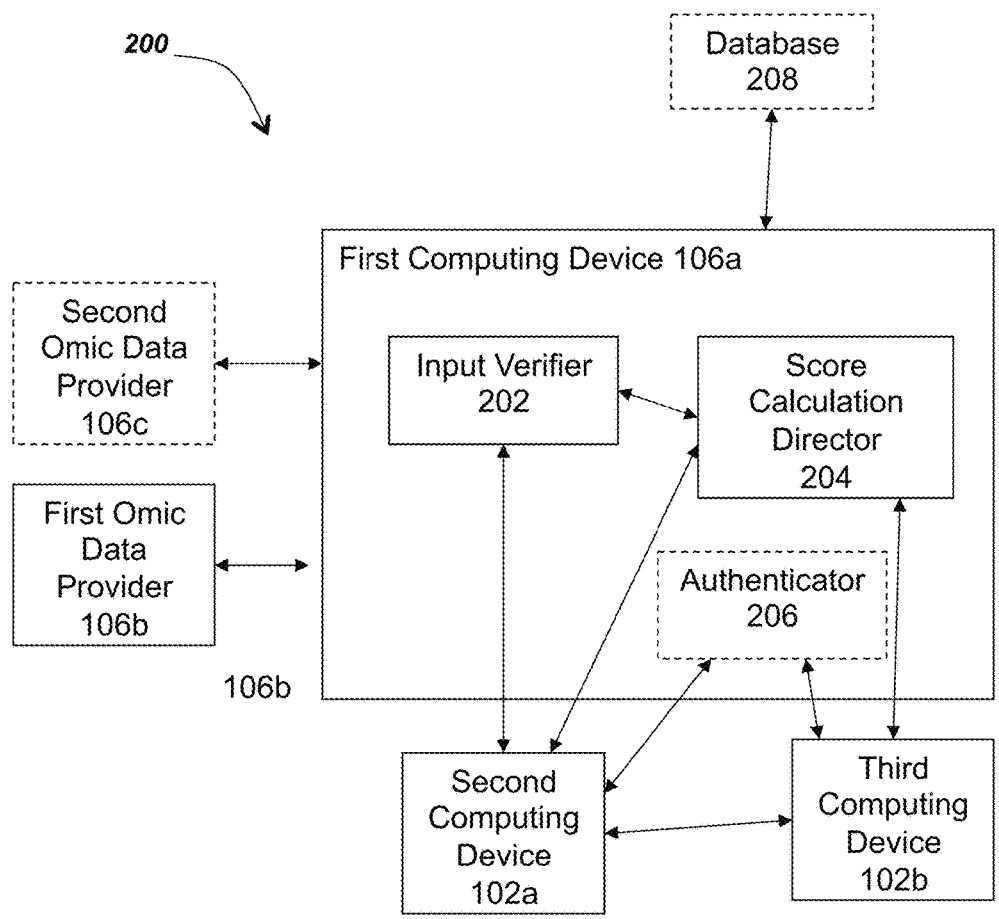
FIG. 2A is a block diagram depicting one embodiment of a system for verifiable, private, and secure omic matching.

Referring now to FIG. 2A, a block diagram depicts one embodiment of a system 200 for verifiable, private, and secure omic matching. In brief overview, the system 200 includes a first computing device 106a. The first computing device 106a may be a computing device 106 as described above in reference to FIGS. 1A-1C. The system 200 also includes an input verifier 202 and a score calculation director 204, each executing on the first computing device 106a.

In some embodiments, the input verifier 202 may be a software program. The input verifier 202 may additionally or alternatively include a hardware module. In some embodiments, the input verifier 202 receives, from a first omic data provider 106b, a first set of verification data. The first omic data provider 106b may be a computing device 106 as described above in reference to FIGS. 1A-1C.

The omic data provider 106b may generate omic data. While many of the systems and methods described herein may be particularly valuable when used in connection with genomic data, it is recognized and understand that many may also be beneficially used in connection with omic data more generally. Omic data is data that profiles a biological organism via detailed analysis of particular biological structures or systems. Omic data may include chemical omic data, which is data describing the structure or function of a particular set of chemical compounds within the biological organism. Omic data may include polymeric sequencing omic data, profiling patterns within polymeric chains found within the biological organism. Some embodiments of omic data contain analysis of sequences of genetic data. In one embodiment, omic data is genomic data. Genomic data may profile at least one nucleotide sequence found in the biological organism that contains the genetic code for producing at least one protein. Nucleotide sequences may include deoxyribonucleic acid (DNA) sequences. Nucleotide sequences may include ribonucleic acid (RNA) sequences. The genetic code may include the encoded amino acid sequence of the protein. The genetic code may include information that guides the formation of the protein; for instance, the genetic code may guide the protein assembly apparatus within the organism to fold the amino acid sequence in a particular way. The genetic code may contain information dictating the frequency with which the protein is produced.

In another embodiment, omic data profiles non-coding nucleotide sequences. For instance, omic data may contain profiles of nucleotide sequences describing cellular lifespans. Omic data may contain profiles of nucleotide sequences dictating cellular differentiation. Omic data may contain profiles of nucleotide sequences that direct the management of nucleotide sequences, such as sequences affecting the processes of meiosis, mitosis, or transposon exchange.

In another embodiment, omic data includes epigenomic data describing a history of chemical changes to the DNA and histone proteins of the biological organism. Omic data may include transcriptomic data, describing the set of RNA molecules produced by the organism, or by a sample from the organism. Omic data may include proteomic data, describing the set of proteins expressed within at least one sample of the biological organism at a particular time. Omic data may include phenomic data, describing the phenotypic attributes of the biological organism. Omic data may include metabolomic data, describing the metabolites found within a sample pertaining to the biological organism. In some embodiments, omic data includes metagenomic data, which describes genomic data derived from a sample taken from the environmental context of the biological organism. Omic data may include microbiomic data; for instance, a tissue sample taken from a person might include nucleotide sequences pertaining to the particular person, as well as sequences pertaining to organisms that coexist with the person in a parasitic or symbiotic context.

In some embodiments, the omic data contains a combination of sets of omic data. For instance, the omic data may combine the proteomic and genomic data of the biological organism. The omic data may combine the genomic data of the biological organism with the epigenomic data of the biological organism. In some embodiments, the omic data includes more than one data set corresponding to a particular category of omic data. For instance, the biological organism may be chimeric, containing more than one genome; the omic data may contain a genomic profile for each genome contained in the chimeric organism. In some embodiments, the omic data contains omic profiles for organisms that live on or within the biological organism; for instance, the omic data may contain a genomic profile of mitochondria living within the cells of a person. The omic data may contain a genomic profile of a separate organism living within the digestive system of a person. The omic data may contain a genomic profile of a non-chromosomal genetic sequence active within the biological organism; for instance, the omic data may contain the genomic profile of a plasmid. The omic data may contain the genomic profile of a virus or other pathogen.

The omic data provider 106b may be a computing device operated by an entity that derives omic data from biological samples. In some embodiments, a sample is any quantity of biological matter from which omic data may be derived. For example, a sample may be a blood sample, tissue sample, or one or more individual cells taken from the biological organism. An entity producing the omic data may analyze the sample to produce the omic data. The entity producing the omic data may analyze more than one sample to produce the omic data for a single biological organism. The omic data provider 106b may compare the omic data pertaining to the biological organism to a representative set of omic data. The omic data provider 106b may select the representative set of omic data from a plurality of representative sets of omic data; for example, the omic data provider 106b may compare specific loci within the omic data to those of one of the plurality of representative sets of omic data, selecting a representative set with a high degree of similarity to the omic data at the specific loci. The omic data provider 106b may store the set of differences between the omic data and the representative set instead of the full set of omic data, to allow greater ease in manipulating and storing the omic data.

In some embodiments, the system 200 processes metadata. Metadata may be any data concerning the omic data, which is not itself omic data. Metadata may include data identifying the biological organism from which the omic data was derived, such as a name, a date of birth, and/or a social security number. In one embodiment, metadata includes data describing the biological organism from which the omic data was derived. Metadata may include biometric data. Metadata may include the eye color of a person, for example. Metadata may describe characteristics of the biological organism. Metadata may describe photographic data concerning the biological organism. Metadata may include demographic metadata describing a population group to which the biological organism belongs; for instance, demographic metadata may describe the sex, age, ethnicity, or national origin of a person.

In another embodiment, metadata includes data concerning the sample from which the omic data provider extracted the omic data. Metadata may include information identifying the nature of the sample. Metadata may include information describing the manner of collection of the sample. Metadata may include a time and date at which the sample was provided. Metadata may include a time and date at which the sample was generated. Metadata may include detail of the originating tissue; for example, metadata may describe the bodily site of origin of the sample. Metadata may describe the disease state of the sample, such as whether the sample is a tumor. Metadata may also include data about the state of the patient at one or more times. For example, the metadata may describe the metabolic state of patient: the time that has elapse since the last meal, how much sleep the patient has been getting, and whether the patient is intoxicated or has been using recreational drugs. Metadata may include the health state of the patient at the time the sample was taken.

System 200 may process verification data. Verification data may be data that the input verifier 202 can use to determine that omic data present on a second computing device 102a is identical to a particular set of omic data produced by the omic data provider 106b, as set forth in more detail below. The verification data may be the omic data. The verification data may be a subset of the omic data. The verification data may be one or more encrypted blocks of omic data.

In some embodiments, the verification data is encrypted by the omic data provider 106b according to a public key cryptosystem. A public key cryptosystem is a cryptosystem that has a publicly available encryption key and a decryption key that is kept private. In a conventional public key cryptosystem, an entity can encrypt a plaintext using the encryption key, but will typically be unable, absent an excessively large amount of time or computing power, to decrypt any message, or even to deduce the decryption key given their (known) plaintext and (recently produced) cyphertext. An example of a public key cryptosystem is RSA, which relies on the empirically observed computational hardness of factoring large numbers that are the product of two large primes. In some embodiments, the public key cryptosystem is homomorphic; a function f(x): X→Y from space X to space Y is homomorphic if f(a+b)=f(a)+f(b) for a given first definition of the operator "+" in X and a given second definition of the operator "+" in Y. For instance, RSA is homomorphic over the multiplicative operator in the plaintext space and the exponentiation operator in the cyphertext space. In some embodiments, the public key cryptosystem is partially homomorphic. In some embodiments, the public key cryptosystem is not homomorphic.

The input verifier 202 may request, from the second computing device 102a, a verification output, as set forth in more detail below. The second computing device 102a may be a computing device 102 as set forth above in reference to FIGS. 1A-1C. The second computing device 102a may be a remote device 106 as described above in reference to FIGS. 1A-1C. The input verifier 202 may determine that the first verification output matches the first set of verification data, as set forth in more detail below.

System 200 includes a score calculation director 204 executing on the first computing device 106a. The score calculation director 204 may be implemented by a software program. The score calculation director may be implemented by a hardware module. In one embodiment, the score calculation director 204 directs a calculation of a matching score by the second computing device 102a and a third computing device 102b, as set forth in more detail below. The third computing device 102b may be a computing device 102 as described above in reference to FIGS. 1A-1C. The third computing device may be a remote device 106 as set forth above in reference to FIGS. 1A-1C. As a non-limiting example, the second computing device 102a may be a computing device 102 operated by a user seeking a sperm donation, while the third computing device 102b may be a remote device 106 operated by a sperm bank. The second computing device 102a may be a virtual machine maintained by a third party (e.g., "located in the cloud"), and the third computing device 102b may be another virtual machine located in the cloud. The third party hosting the virtual machine representing the second computing device 102a may be distinct from the third party hosting the virtual machine representing the third computing device 102b. The second computing device 102a may be a computing device 102 operated by a doctor searching for potential organ donations on behalf of a patient, and the third computing device 102b may be a remote machine 106 operated by a hospital in possession of an organ available for donation. In one embodiment, the second computing device 102a is a computing device 102 used by one user seeking a romantic partner, while the third computing device 102b is another computing device 102 used by a second user seeking a romantic partner.

A matching score may be any score in which a set of omic data is compared to another set of omic data to assess the probability of a particular outcome for a biological organism. In one embodiment, the matching score is a reproductive compatibility score that reflects the likely result if two or more people represented by two or more sets of omic data produce a child together. For instance, a reproductive compatibility score may calculate the probability that a mother and father will produce a child with a genetic disorder, given the genome of the father and the genome of the mother. A reproductive compatibility score may calculate the probability that the child will be tall. A reproductive compatibility score may combine the prospective father's omic data with the prospective mother's omic data to predict the likelihood of a healthy pregnancy; for instance, the mother's proteomic or epigenomic data may affect the probability of healthy fetal development. A reproductive compatibility score may also assess the suitability of a sperm or egg donation for a person wishing to conceive a child using the donated gamete. The matching score may take into account haplotypes either by direct genotyping or by simulating recombination by using known or estimated recombination rates at different genomic sites.

In some embodiments, the reproductive compatibility score includes a calculation of the probability of progeny inheriting different genotypes at a locus given the parents' genotypes. These may be calculated based on simple Mendelian assumptions of segregation and independent assortment. This analysis may be extended to take into account known linkage disequilibrium patterns between different loci. Sequencing technologies may further enable refined haplotype determination and inheritance patterns. Other embodiments include calculation of the probability of manifestation of a certain grade of the disease given inherited genotypes at one or multiple loci. Knowledge about the risk associated with different alleles (which may be expressed in a metric such as Odds Ratio (OR)), their modes of inheritance (autosomal, sex-linked) and the nature of their interaction with other alleles (dominant, recessive, co-dominant, incomplete-dominant) may determine this term. Still other embodiments may involve calculation of severity of disease grade. An a priori relative numeric weight may be assigned to each grade of every disease based on their known or perceived detrimental value to longevity, health, and well-being.

In another embodiment, the matching score is an organ donation compatibility score, which predicts the likelihood of a successful donation of biological matter having one omic profile to a biological organism having a second omic profile. The biological matter may be an internal organ. The biological matter may include an external organ, such as hair, skin, or nails. The biological matter may be tissue. The biological matter may be one or more cells. The biological matter may be a substance, such as blood plasma. In still another embodiment, the matching score is a relatedness score, determining the degree of relatedness of two biological organisms. For instance, a relatedness score may demonstrate that two genomes possess a common mutation suggesting a common ancestor. A relatedness score may determine fraternity. A relatedness score may determine paternity. A relatedness score may also demonstrate sufficient similarity between mitochondrial DNA to determine common ancestry. A relatedness score may also assess similarity between Y-chromosome DNA. The relatedness score may determine the degree of relatedness of one living person to another. The relatedness score may determine the degree of relatedness of a living person to a possible ancestor.

In some embodiments, the matching score is a disease risk assessment score, matching the omic data of a biological organism to a data set associated with the probability of developing one or more illnesses. For example, the genome of a person may be compared to the genome of another person who is known to have developed a particular illness, or to the genome of another healthy person. The genome of a person may be compared to a dummy genome created to represent alleles that are risk factors for a particular illness. In some embodiments, the matching score is a disease condition assessment score, which depicts the probability that the biological organism associated with a particular omic data set currently has one or more illnesses. For example, comparison of a person's blood proteome to a dummy proteome could reveal that the person has an early stage of cancer, allowing for earlier intervention and a better prognosis. In a further example, a disease risk assessment score or disease condition assessment score may anonymously disqualify a prospective participant in a clinical trial, sparing the participant potential embarrassment, and improving the accuracy of the trial.

The matching score may be associated with a biological description. In an embodiment, a biological description is a verbal description identifying the significance of a particular matching score. The biological description may describe a phenotypic characteristic. The biological description may describe a disease condition. The biological description may describe a degree of severity of a disease condition. The biological description may describe a grade of a disease condition. The biological description may indicate the probability of a particular phenotypic expression.

In some embodiments, the system 200 provides functionality for performing secure multiparty computations. In some embodiments, a secure multiparty computation is a calculation that allows two or more parties to jointly calculate the output of a function over their inputs to the function, without revealing to each other or to any other party what their inputs are. The secure multiparty computation protocols may be info-theoretically secure, meaning that an adversary with unlimited computational power (operating within given assumptions) would be unable to discover any party's inputs. Other secure multiparty computation protocols may be secure as long as an adversary is assumed to be constrained to certain computational bounds. The system 200 and participating computing devices may perform a secure multiparty computation using a calculation descriptor. In one embodiment, a calculation descriptor is a data structure that presents the calculation to be performed via secure multiparty computation in an abstract form, which may be shared among parties to the secure multiparty computation. The calculation descriptor may be a Boolean circuit. In some embodiments, a Boolean circuit is the design for a circuit of Boolean logic gates, such as AND, OR, XOR, and NOT gates, the evaluation of which would together produce the result to be calculated, given the inputs of the parties to the secure multiparty computation.

As a non-limiting example of a Boolean circuit, and by way of illustration, consider two persons, John and Mary, who wish to discover the probability that a child they would produce together would develop a particular recessive genetic condition, in the classical Mendelian sense. Assume that the allele associated with the recessive condition is denoted "T" and all alleles not associated with the condition are denoted N. Thus for instance if John has allele set g(J)=NT, and Mary has allele set g(M)=NT, Mendelian calculation shows a 25% probability that a child of Mary and John would have the allele TT, and thus manifest the recessive condition. There is also a 50% probability that the child will be a non-symptomatic carrier, with an allele equal to NT, and a 25% probability that the child will be a non-carrier with an allele of NN. Generalizing to all possible allele combinations of John and Mary, it is possible to write a truth table as follows:

| g(J) | g(M) | Probability of Symptomatic Expression |
|---|---|---|
| NN | NN | 0% |
| NN | NT | 0% |
| NN | TT | 0% |
| NT | NN | 0% |
| NT | NT | 25% |
| NT | TT | 50% |
| TT | NN | 0% |
| TT | NT | 50% |
| TT | TT | 100% |

It is possible to encode the four possible probabilities (0%, 25%, 50%, and 100%) presented by this calculation as two binary bits, with 11 representing a 100% chance of the child being symptomatic, 10 representing a 50% chance of symptoms, 01 representing a 25% chance of symptoms, and 00 representing a 0% probability of symptoms. With the calculation outcomes represented in that bit encoding, the above truth table may be represented as follows, with $g_1(J)$ and $g_2(J)$ signifying the two alleles carried by John, $g_1(M)$ and $g_2(M)$ representing the two alleles carried by Mary, $OP_1$ and $OP_2$ representing the two output bits, an input of 0 representing the allele descriptor N, and an input of 1 representing the allele T:

| $g_1(J)$ | $g_2(J)$ | $g_1(M)$ | $g_2(M)$ | $OP_1$ | $OP_2$ |
|---|---|---|---|---|---|
| 0 | 0 | 0 | 0 | 0 | 0 |
| 0 | 0 | 0 | 1 | 0 | 0 |
| 0 | 0 | 1 | 0 | 0 | 0 |
| 0 | 0 | 1 | 1 | 0 | 0 |
| 0 | 1 | 0 | 0 | 0 | 0 |
| 0 | 1 | 0 | 1 | 0 | 1 |
| 0 | 1 | 1 | 0 | 0 | 1 |
| 0 | 1 | 1 | 1 | 1 | 0 |
| 1 | 0 | 0 | 0 | 0 | 0 |
| 1 | 0 | 0 | 1 | 0 | 1 |
| 1 | 0 | 1 | 0 | 0 | 1 |
| 1 | 0 | 1 | 1 | 1 | 0 |
| 1 | 1 | 0 | 0 | 0 | 0 |
| 1 | 1 | 0 | 1 | 1 | 0 |
| 1 | 1 | 1 | 0 | 1 | 0 |
| 1 | 1 | 1 | 1 | 1 | 1 |

Figure 2B:
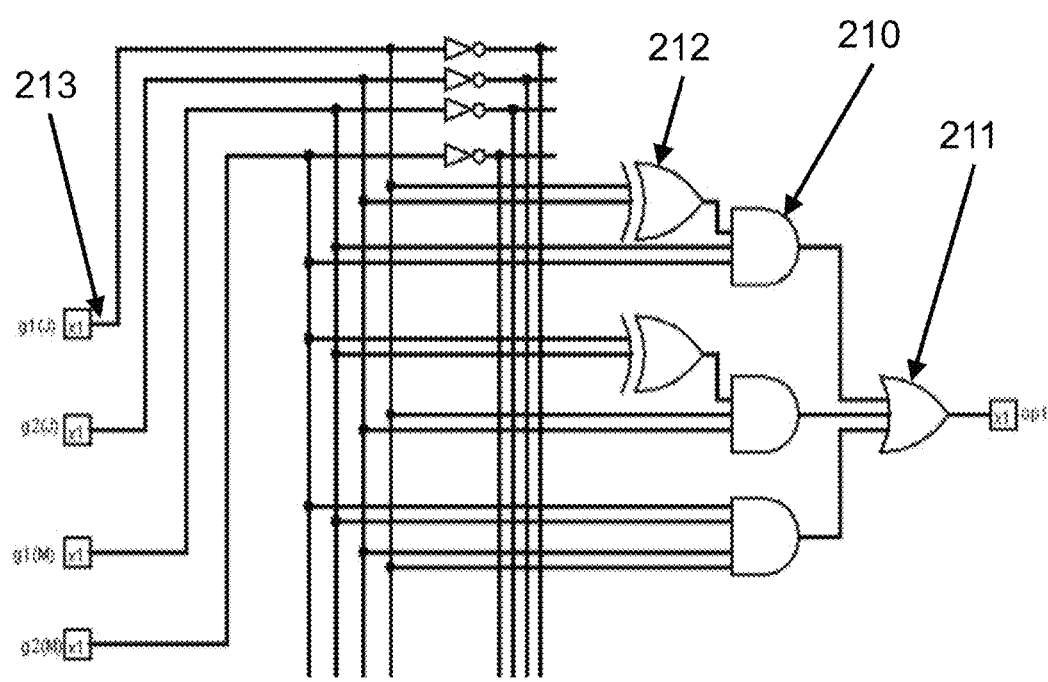
FIG. 2B is a schematic diagram of a Boolean circuit associated with a simple truth table relating to an omic calculation.
Figure 2C:
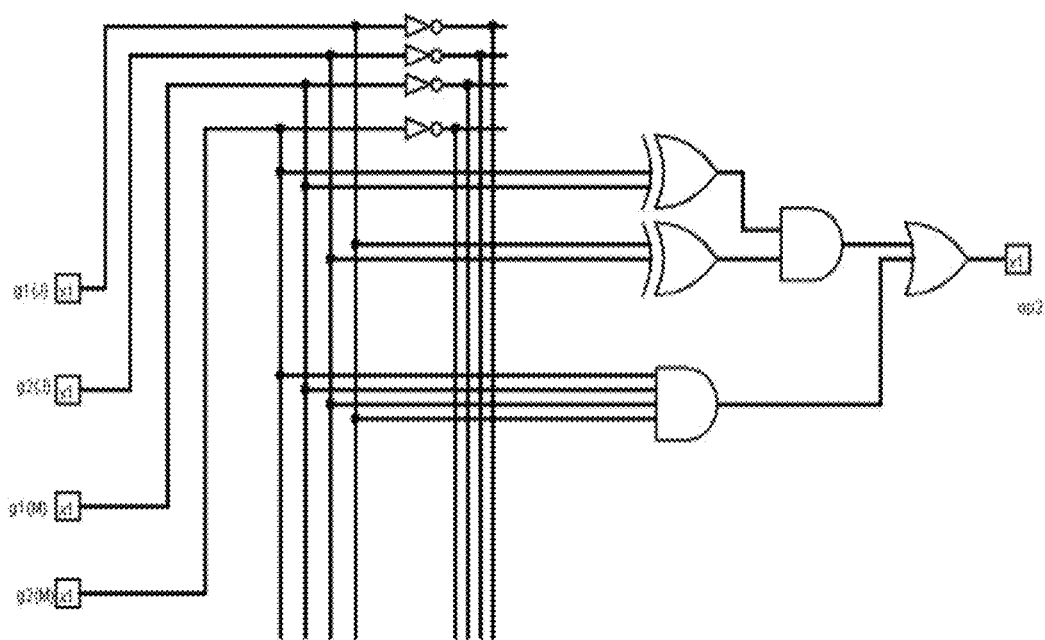
FIG. 2C is a schematic diagram of a Boolean circuit.

FIG. 2B illustrates the Boolean circuit that calculates the first output bit. The gates in the circuit are designed to produce the outcomes for each set of inputs, as dictated by the above truth table, in a compact and computationally efficient manner; careful evaluation of each AND gate 210, OR gate 211, and XOR gate 212, shows that the circuit produces the same outputs as the above truth table. FIG. 2C illustrates a Boolean circuit that calculates the second output bit.

In embodiments attempting to predict the probability of several different genetic conditions, a larger truth table and a correspondingly larger Boolean circuit is used. Likewise, in embodiments where the inheritance pattern of a condition differs, a different truth table results, as well as a different circuit. Although for the sake of simplicity, the truth table and Boolean circuit for a single recessive phenotype is depicted here, a Boolean circuit can represent any calculation that a computer may perform, because by definition any such calculation would be performed on a computer by a series of Boolean gate evaluations.

Some embodiments of the system 200 provide functionality for exchanging secure shares. In one embodiment, a secure share is a datum that a party to a secure multiparty computation provides to the other parties to the secure multiparty computation, having the properties that the secure shares used by all parties to the computation, taken together, permit the computation to produce the desired output, while the possession by any party of less than all of the secure shares will not enable that party to deduce the inputs of the other parties to the secure multiparty computation. As a result, at least a subset of the secure shares can be freely exchanged, within the bounds of the protocol, without compromising the data privacy of any party. Some secure shares are info-theoretically secure, meaning that an adversary with unlimited computing power could never use the secure share to deduce the value of the input on which the secure share was based. Other secure shares are secure against adversaries whose computational power is less than some specified limit.

As a non-limiting example for the creation and use of secure shares, consider a gate with two input wires, and inputs $s_{00}$, $s_{01}$, $s_{10}$, and $s_{11}$ corresponding to the four possible inputs to the wire; the first party, herein denoted "Mary," creates two random strings $R_0$ and $R_1$, which will be the shares for the first input wire, and creates a share consisting of $s_{00} \oplus R_0$ concatenated with $s_{10} \oplus R_1$ to represent the 0 input to the second input wire, an another share consisting of $s_{01} \oplus R_1$ concatenated with $s_{11} \oplus R_1$, where order of the concatenations may be reversed according to a randomly generated bit for added security; the symbol $\oplus$ in this example denotes the logical operation XOR. Continuing the example, the second party to the calculation, herein denoted "John," obtains, via oblivious transfer, one share for each input wire; John then extracts bit b from the first block of the first input wire's share and bit r from the second block of the first input wire's share, selects bit a which is the $b^{th}$ block of the second input wire's share, then computes $r \oplus a$ to derive the input to be used for the wire corresponding to Mary's input. In some embodiments, implementation of the methods and systems described herein leverages the solutions discussed in Ronald L. Rivest, *Unconditionally Secure Commitment and Oblivious Transfer Schemes Using Private Channels and a Trusted Initializer* (MIT November 1999).

In some embodiments, the system 200 performs oblivious transfers. As will be understood by one of ordinary skill in the art, an oblivious transfer is a transfer in which one party to a secure multiparty computation conveys at least one of a plurality of secure shares to another party to the secure multiparty computation, without knowing which of the two secure shares has been conveyed. Some oblivious transfers are info-theoretically secure. An example of an info-theoretically secure oblivious transfer from one party ("Mary") to another party ("John") involves the intercession of a trusted third party ("Charlie"); each party may be a computing device as described above in reference to FIGS. 1A-1C. In this example, Charlie privately gives Mary two random k-bit strings $r_0$ and $r_1$, for some natural number k; Charlie flips a bit d and privately gives John d and $r_d$ (i.e., if d=0, Charlie provides John with $r_0$, and if d=1, Charlie provides John with $r_1$). Continuing with this example, John determines his input c; he wants share $m_c$ from Mary corresponding to his input c, and he privately sends Mary $e = c \oplus d$, where "e" is the Boolean operator XOR. Continuing with this example, Mary computes two secure shares $m_0$ and $m_1$ and privately sends John the values $f_0 = m_0 \oplus r_e$, $f_1 = m_1 \oplus r_{(1-e)}$; John computes $m_c = f_c \oplus r_d$. In some embodiments oblivious transfer is a committed oblivious transfer, in which one or both of the parties to the transfer commits to the values to be transferred, so that if the oblivious transfer is interrupted, for instance by a network outage, and later resumed, no party can receive further information by modifying its inputs.

In some embodiments, the system 200 also includes an authenticator 206, executing on the first computing device 106a. The authenticator 206 may be a software program. The authenticator 206 may be a hardware module. In some embodiments, the authenticator 206 authenticates omic data, as set forth in more detail below.

In some embodiments, the first computing device 106a is in communication with a database 208. The database 208 may be a relational database. The database may be a key-value database. In some embodiments, the database 208 is an ODBC-compliant database. For example, the database 208 may be provided as an ORACLE database, manufactured by Oracle Corporation of Redwood Shores, Calif. In other embodiments, the database 208 can be a Microsoft ACCESS database or a Microsoft SQL server database manufactured by Microsoft Corporation of Redmond, Wash. In still other embodiments, the database may be a custom-designed database based on an open source database, such as the MYSQL family of freely available database products distributed by MySQL AB Corporation of Uppsala, Sweden. In some embodiments, the database 208 is maintained by, or associated with, a third party.

Verifiable, Private and Secure Omic Matching

Figure 3:
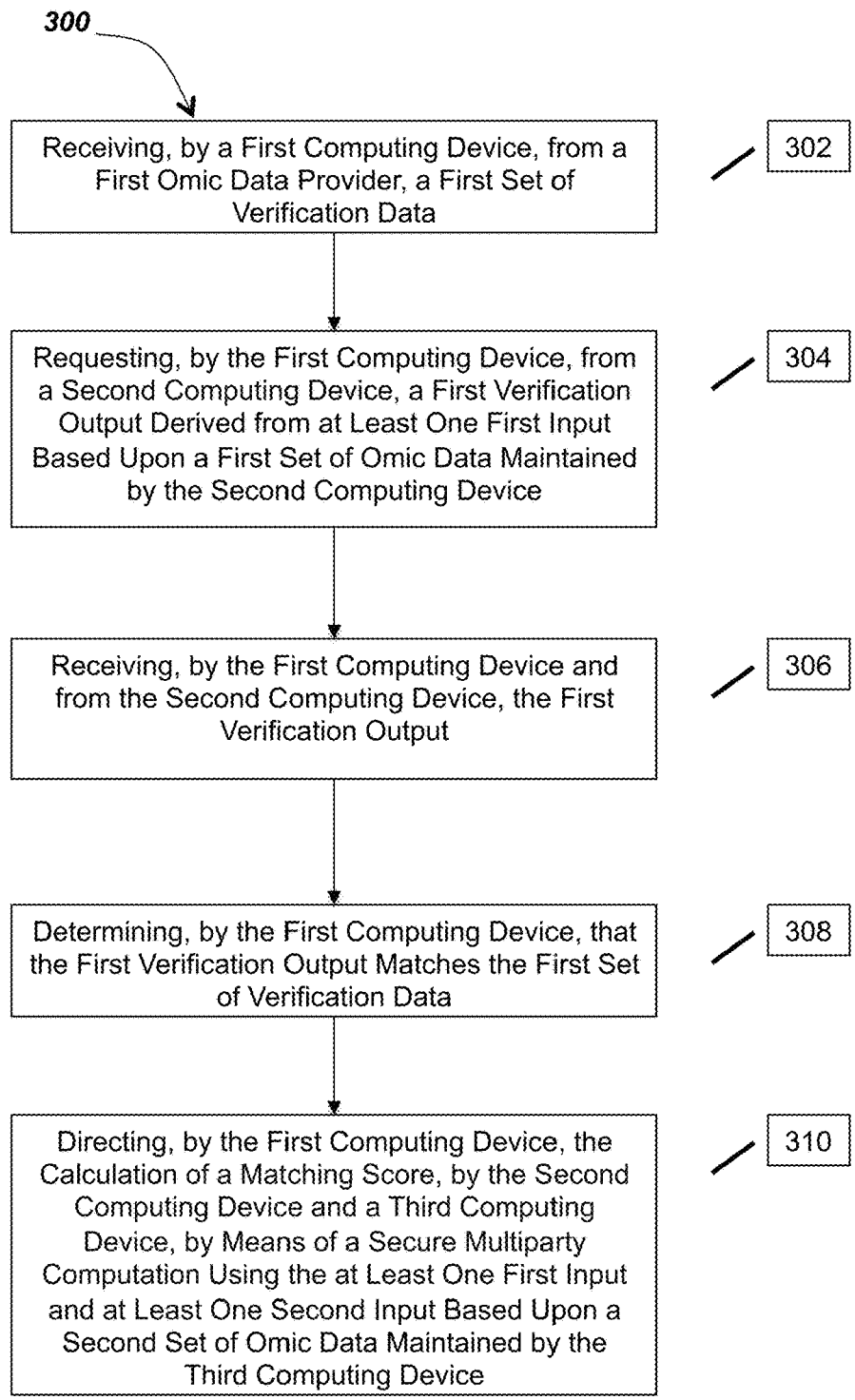
FIG. 3 is a flow diagram depicting an embodiment of a method for verifiable, private, and secure omic matching.

Referring now to FIG. 3, a flow diagram depicts one embodiment of a method for verifiable, private, and secure omic matching. In brief overview, the method includes receiving, by a first computing device, from a first omic data provider, a first set of verification data (302). The method includes requesting, by the first computing device, from a second computing device, a first verification output derived from at least one first input based upon a first set of omic data maintained by the second computing device (304). The method includes receiving, by the first computing device and from the second computing device, the first verification output (306). The method includes determining, by the first computing device, that the first verification output matches the first set of verification data (308). The method includes directing, by the first computing device, the calculation of a matching score, by the second computing device and a third computing device, by means of a secure multiparty computation using the at least one first input and at least one second input based upon a second set of omic data maintained by the third computing device, responsive to the determination that the first verification output matches the first set of verification data (310).

Referring now to FIG. 3 in greater detail, and in connection with FIG. 2A, the method 300 includes receiving, by a first computing device, from a first omic data provider, a first set of verification data (302). In some embodiments, the first omic data provider 106b provides omic data; for instance, the omic data provider may provide the entire first set of omic data. In some embodiments, the omic data provider 106b provides verification tags that are derived from the omic data but do not permit the first computing device 106a to determine the contents of the omic data. For instance, the omic data provider 106b may divide the omic data into unique blocks of data, and then encrypt each block of data using a homomorphic public key cryptosystem. The first computing device 106a may use the encrypted blocks of data to verify inputs from the second computing device 102a as described in more detail below.

The first computing device 106a may store the verification data in memory accessible to the first computing device 106a. The first computing device 106a may store the verification data in a database 208. In some embodiments, the verification data is arranged according to a hash function, so that the first computing device 106a can rapidly retrieve it. In some embodiments, the omic data generator 106b sends the first computing device 106a information allowing it to determine to which locus a given encrypted block of encrypted omic data pertains.

The method includes requesting, by the first computing device, from a second computing device, a first verification output derived from at least one first input based upon a first set of omic data maintained by the second computing device (304). In some embodiments, the first computing device 106a authenticates a user of the second computing device 102a prior to requesting the first verification output. The first computing device 106 may require the user to submit an answer to a challenge question; for instance, the user may have to enter a password. In some embodiments, the user is authenticated by the authenticator 206 as set forth in more detail below. The first computing device 106a may create a session persisting the identity of the second computing device 102a, along with any authentication information, until the conclusion of the method.

In one embodiment, where the verification data includes blocks of omic data encrypted under a homomorphic public key cryptosystem, the input verifier generates a challenge string by producing a random number in the plaintext space, and encrypting that random number using the publically available encryption key. For instance, where the cryptosystem is RSA, the omic data provider 106b may provide a public encryption key containing N, which is a large number that is the product of two large primes, a number g, which is a generator of the group of quadratic residues modulo N, and a set of blocks of encrypted data $D_i = g^{m_i} \mod N$, where $m_i$ are the blocks of omic data. In some embodiments, the omic data provider 106b does not share the decryption key with the first computing device 106a, so that the first computing device 106a will be unable to use those blocks $D_i$ to determine the contents of the original omic data unless it can break the public key encryption. The first computing device 106a may generate a challenge string by generating a random number s in the integers mod N, computing $g_s = g^s \mod N$, and sending $g_s$ to the second computing device 102a. In some embodiments, implementation of the methods and systems described herein leverages the solutions discussed in Zhuo Hao, et al., *A Privacy-Preserving Remote Data Integrity checking Protocol with Data Dynamics and Public Verifiability*, Knowledge and Data Engineering, IEEE Transactions on, v 0.23, no. 9, pp. 1432, 1437 (September 2011).

The first computing device 106a may also specify the loci corresponding to which the input data is to be verified. As the knowledge required to associate specific loci with particular biological phenomena is general in nature, the first computing device 106a may specify the loci to verify without possessing any information specific to the omic data from which the verification data is derived.

The method includes receiving, by the first computing device and from the second computing device, the first verification output (306). In some embodiments, the second computing device 102a creates the first verification output by encrypting a block of omic data and transmitting the encrypted block to the first computing device 106a. As will be understood by those of ordinary skill in the art, if the second computing device 102a uses the same public encryption key used to create the verification data to encrypt the verification output, the first computing device 106a may determine that a block of omic data encrypted in the verification output is identical to a block of omic data encrypted in the verification data without decrypting either block, because the encrypted forms of two identical data that have been encrypted using identical instances of a cryptosystem will also be identical in many cryptosystems. Where the input verifier 202 requested the verification output using an encrypted challenge string, the second computing device 102a may combine the encrypted challenge string with an encrypted block of omic data. For instance, where the first computing device sent a challenge string $g_s = g^s \mod N$ as described above in reference to step 304, the first verification output may include $D'_i = g_s^{m_i} \mod N$, where $m_i$ is the at least one input. The second computing device 102a may create the verification output using a block of omic data indicated by the input verifier 202.

The second computing device 102a can send the first computing device the verification output by any means for communication over the network described above in reference to FIGS. 1A-1C. In some embodiments, the second computing device 102a sends the first computing device 106a the verification output via a secure channel protocol, such as Secure Shell. In some embodiments, the second computing device 102a sends the first computing device 106a the verification output by means of a secure multiparty computation, so that the first computing device 106a can receive the verification output without being able to discover the data used to create the verification output. In some embodiments, the input verifier 202 receives the first verification output by obtaining a verification calculation descriptor and calculating, with the second computing device, the verification output using the verification calculation descriptor. The input verifier 202 may create the verification calculation descriptor. The second computing device 102a may create the verification calculation descriptor. A third-party device (not shown) may create the verification calculation descriptor. In some embodiments, the verification output descriptor is a Boolean circuit, as described above in reference to FIGS. 2A-2C. The Boolean circuit may be a Boolean circuit the evaluation of which, when evaluated, converts the at least one input into the verification output; for instance, the Boolean circuit, when evaluated jointly by the input verifier 202 and the second computing device 102a, may encrypt the at least one input $m_i$ by calculating $D'_i = g_s^{m_i} \mod N$, as described above.

The input verifier 202 and second computing device 102a may compute the verification output using a garbled circuit protocol, such as Yao's Garbled Circuits, which are well-understood by persons of ordinary skill in the art. The input verifier 202 and second computing device 102a may compute the verification output using a gate evaluation secret sharing (GESS) protocol such as those familiar to persons of ordinary skill in the art. As an example, the Boolean circuit used as the verification calculation descriptor may take inputs from the first computing device 106a corresponding to its challenge string as described above, while its inputs corresponding to the second computing device 102a may correspond to the at least one input $m_i$ provided by the second computing device 102a.

The input verifier determines that the first verification output matches the first set of verification data (308). In some embodiments, where the verification data was created by the omic data provider by encrypting blocks of omic data using a public key encryption system, and the verification output contained encrypted blocks of omic data as well, the input verifier 202 compares the verification output to the encrypted blocks provided by the omic data provider 106b. As noted above, the first computing device 106a may do this by directly comparing the two encrypted blocks of data, without being able to decrypt either block. Where the input verifier 202 requested the verification output using a challenge string generated by encrypting a random number, the input verifier 202 may use the encryption algorithm to add the challenge string to the encrypted block of omic data, and may verify that the result matches the verification output created by combining the encrypted challenge string with the block of unencrypted data. As an example, where the verification tags are of the form $D_i = g^{m_i} \mod N$ as described above, the input verifier computes $D''_i = D_i^s \mod N$; if $D''_i = D'_i$, the input $m_i$ must match the block of omic data used by the omic data provider 106b to create $D_i$, due to the homomorphic nature of the cryptosystem. As before, the possession of $D''_i$ and of $D'_i$ by the first computing device 106a will be recognized by skilled practitioners as insufficient to discover the contents of $m_i$ without the decryption key or sufficient computational power to break the encryption. In some embodiments, the comparison of verification data to the verification output is itself performed via a secure multiparty computation, the output of which indicates only either that the verification data matches or does not match the verification output. In some embodiments, the verification data and verification output are encrypted using multiple keys. In some embodiments the verification data and verification output are encrypted using multiple encryption systems. The encryption systems may be homomorphic. The encryption systems may be partially homomorphic. The encryption systems may be non-homomorphic. Where each layer of encryption is homomorphic, the examples above concerning the use of homomorphic encryption systems are applicable to the encryption as a whole, because homomorphism is preserved under function composition (i.e., if f:X-Y is homomorphic, and g:Y-Z is homomorphic, then g(f):X-Z is also homomorphic, if the same operators are used in the same spaces), the verification methods described above in reference to FIG. 3 are applicable.

The method includes directing, by the first computing device, the calculation of a matching score, by the second computing device and a third computing device, by means of a secure multiparty computation using the at least one first input and at least one second input based upon a second set of omic data maintained by the third computing device (310). The use of secure multiparty computation to compute the matching score ensures that the third computing device 102b will be unable to discover the data input to the calculation by the second computing device 102a. Likewise, the second computing device will be unable to deduce the inputs from the third computing device 102b to the calculation. In addition, the inputs of both devices will be secure against the first computing device 106a, as well as any third-party device (not shown). In some embodiments, the second computing device 102a uses at least one first input to create the verification output at substantially the same time that the second computing device 102a uses the at least one first input in the secure multiparty computation. For instance, where the second computing device 102a transmits the verification output to the input verifier 102a by means of a secure multiparty computation protocol, each secure share submitted by the second computing device 102a to the secure multiparty computation producing the verification output may be identical to a secure share submitted by the second computing device 102a to the secure multiparty computation producing the matching score.

In some embodiments, each secure share is transmitted substantially simultaneously to the third computing device 102b and to the input verifier 202. In other embodiments, the shares are transmitted to the third computing device 102b and the input verifier 202 at different times. In still other embodiments, the shares are transmitted to the third computing device 102b and to the input verifier 202 in different orders. For instance, the input verifier 202 and score calculation director 203 may run their respective calculations in parallel, with the score calculation director 203 pausing prior to completing calculation at a particular locus until the input verifier 202 has verified the inputs pertaining to that locus. In some embodiments, the third computing device 102b also transmits each share it receives to the first computing device 106a so that the first computing device 106a can check that the input verifier 202 is receiving the same inputs as the matching score calculation. The input verifier 202 may thus be able to determine that the omic data to be verified is identical to the omic data used to calculate the matching score, without being able to discover the contents of the omic data itself.

In some embodiments, the score calculation director 204 produces a calculation descriptor for use in the secure multiparty computation used to calculate the matching score. In some embodiments, the second computing device 102a produces the calculation descriptor. In some embodiments, the third computing device 102b produces the calculation descriptor. In some embodiments, a third-party device (not shown) produces the calculation descriptor. The calculation descriptor used in the calculation of the matching score may be combined with the calculation descriptor used to calculate the verification output, causing the verification output production and the matching score calculation to be a single secure multiparty computation involving the first computing device 106a, the second computing device 102a, and the third computing device 102b. Those of ordinary skill in the art will understand that the information used to create the calculation descriptor need not depend on knowledge concerning either set of omic data. For instance, to create the Boolean circuit described above in reference to FIGS. 2B and 2C, only general knowledge concerning the locus of the recessive genotype to be detected is necessary; neither John nor Mary's genome need be known to create the circuit; conversely, possession of the circuit does not make it possible for any party to deduce anything concerning John's genome or Mary's genome.

In some embodiments, the secure multiparty computation used to calculate the matching score further includes a garbled circuit protocol. The garbled circuit protocol may be a version of Yao's Garbled Circuits. The garbled circuit protocol may be a GESS protocol. In some embodiments, the second computing device 102a derives at least two secure shares for each input the second computing device 102a has for an input wire. The second computing device transmits one of the at least two shares to the third computing device 102b via an oblivious transfer, as defined above in reference to FIGS. 2A-2C. The third computing device 102b uses the received secure share and its input to calculate the output of the gate to which the wire corresponds. In some embodiments, that process is repeated for each gate until the complete circuit has been evaluated. In some embodiments, the third computing device 102b generates the secure shares, and the second computing device 102a receives the secure shares. In some embodiments, the second computing device 102a generates the secure shares for some gates and the third computing device 102b generates the secure shares for other gates. In some embodiments, the second computing device 102a generates the secure shares for some output bits and the third computing device 102b generates the secure shares for other output bits. The score calculation director 204 may randomly assign roles to the second computing device 102a and the third computing device 102b for each separate evaluation.

As a non-limiting example, the second computing device 102a may call an algorithm to generate shares for the inputs of a Boolean circuit, such as the one depicted in FIG. 2B. Continuing the example, once the second computing device 102a calls the algorithm first to generate shares corresponding to the input wires of the final gate 211 in the circuit; as each input share is associated with the output of another gate 210 farther up the circuit, the second computing device 102a may call the algorithm for each gate 210 that outputs the inputs to the gate 211 just evaluated, and continue the recursion until deriving the secure shares corresponding to the inputs of each gate 212 receiving an input 213 to the circuit. Further continuing the example, the second computing device 102a sends the secure shares corresponding to the circuit inputs to the third computing device 102b via an oblivious transfer as described above in reference to FIGS. 2A-2C; the second computing device 102a may send the same secure shares to the first computing device 106a as well, for computation of the verification output as discussed above in reference to FIG. 3. Continuing the example, the third computing device 102b uses its inputs and the shares it receives to evaluate each input gate 212, and uses the resulting outputs to evaluate each gate 211 farther down the circuit, concluding by evaluating the final output gate 210 to calculate an output bit for the circuit. In the above example, the process may be repeated for each output bit. The process may be repeated for each locus of interest in the calculation. In some embodiments, the third computing device 102b generates the secure shares and the second computing device 102a receives the secure shares via oblivious transfer. The second computing device 102a and third computing device 102b may switch roles for each output bit. The second computing device 102a and the third computing device 102b may switch roles for each locus of interest.

In some embodiments, the garbled circuit protocol further includes a redundancy-based protocol for neutralizing malicious circuits. For instance, in some embodiments, the algorithm includes a cut-and-choose protocol familiar to skilled practitioners, in which the computing device that created the Boolean circuit creates a plurality of Boolean circuits each with a different set of XOR gates added prior to the input wires, in varying patterns, such that the evaluation of each Boolean circuit thus created will produce an identical output given identical inputs. Another party to the secure multiparty computation may select a subset of the various Boolean circuits to calculate its output, and the secure multiparty computation may proceed with each of the Boolean circuits in the subset. The score produced by the majority of the Boolean circuits in the selected subset may be adopted as the correct matching score, unless during the evaluation of the redundant circuits it becomes apparent that the majority of the Boolean circuits have been maliciously constructed to enable the constructor to deduce the other party's underlying data. In some embodiments, the oblivious transfer protocol is an info-theoretic oblivious transfer using a trusted third party, as described above in reference to FIGS. 2A-2C. The trusted third party may be the first computing device 106a. In some embodiments, the garbled circuit protocol involves a committed oblivious transfer protocol, as described above in reference to FIGS. 2A-2C. In some embodiments, the secured multiparty computation contains safeguards against volume-based automated attacks; for example, a user may be required to input characters from an image that is non-machine readable before the secure multiparty calculation initiates. The system may require each user to enter explicit permission for each distinct calculation. Where the metadata is biometric, the system may require the user to submit a biometric sample for each calculation. The computation may prevent volume based attacks through the deliberate introduction of noise. The computation may prevent volume based attacks by levying a small automatic payment for each computation, making large numbers of computations required for a volume based attack financially unattractive.

Figure 2D:
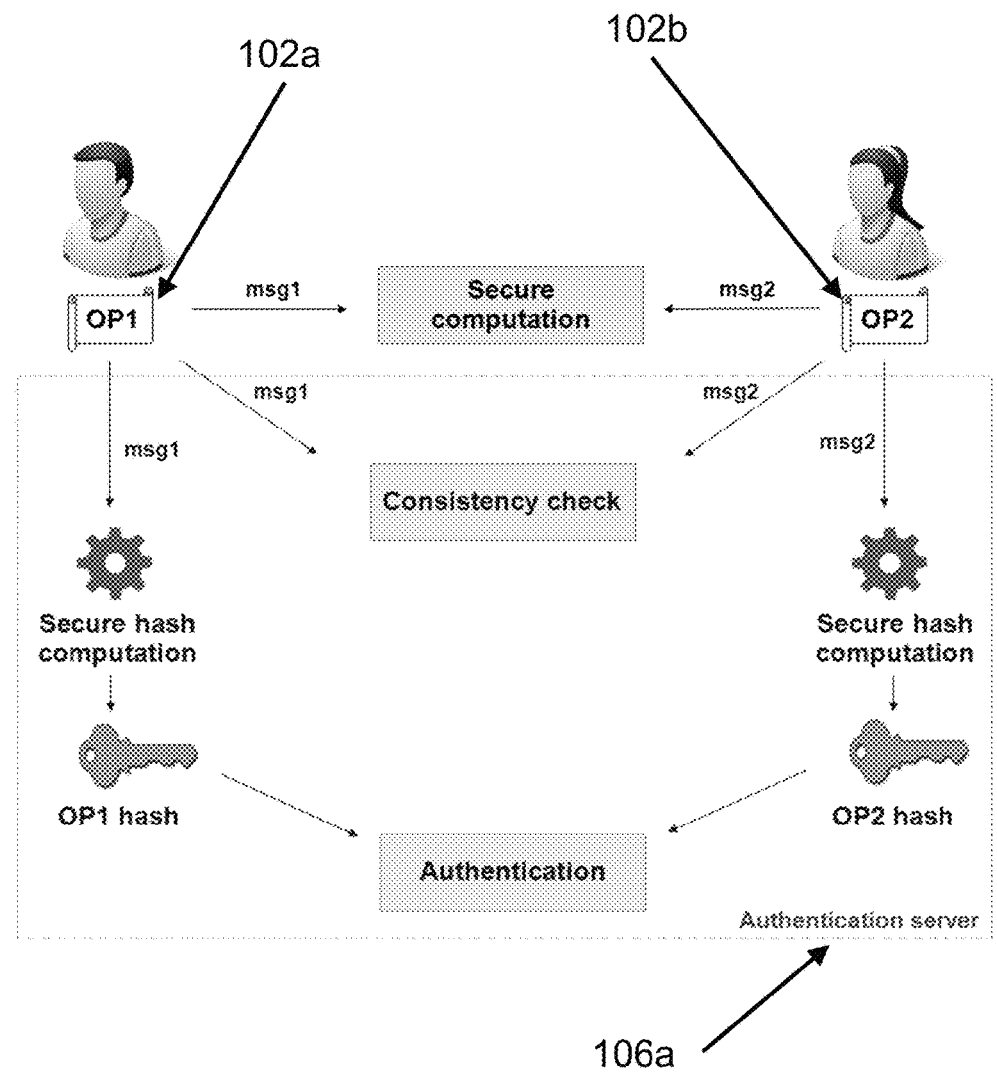
FIG. 2D is a schematic diagram depicting an embodiment of the disclosed system.

FIG. 2D depicts another embodiment of the system 200 providing functionality for executing the method 300 described in further detail below. The first computing device 106a functions as an authentication server, verifying inputs by the second computing device 102a and the third computing device 102b to the secure multiparty computation by checking that each input to be verified is consistent with the input submitted to the secure multiparty computation, and by authenticating each input, as set forth in more detail below.

In one embodiment, the score calculation director 204 directs the calculation of a reproductive compatibility score, by the second computing device and a third computing device, by means of a secure multiparty computation using the at least one first input and at least one second input based upon a second set of omic data maintained by the third computing device. In another embodiment, the score calculation director 204 directs the calculation of an organ donation compatibility score, by the second computing device and a third computing device, by means of a secure multiparty computation using the at least one first input and at least one second input based upon a second set of omic data maintained by the third computing device. In an additional embodiment, score calculation director 204 directs the calculation of a relatedness score, by the second computing device and a third computing device, by means of a secure multiparty computation using the at least one first input and at least one second input based upon a second set of omic data maintained by the third computing device. The score calculation director 204 may direct the calculation of a disease risk assessment score, by the second computing device and a third computing device, by means of a secure multiparty computation using the at least one first input and at least one second input based upon a second set of omic data maintained by the third computing device. The score calculation director 204 may direct the calculation of a disease condition assessment score, by the second computing device and a third computing device, by means of a secure multiparty computation using the at least one first input and at least one second input based upon a second set of omic data maintained by the third computing device.

The score calculation director 204 may direct a score calculation that uses a subset of each set of omic data. For instance, the score calculation director 204 may retrieve from memory accessible to the first computing device 106a a list of loci related to typical areas of concern for the matching score calculation in question. Thus, for instance, in a reproductive compatibility calculation, the score calculation director 204 may retrieve a list of genetic loci associated with known genetic disorders. The score calculation director 204 may direct a calculation that uses the retrieved loci. Where the metadata describing the biological organism to which the omic data pertain indicate a likely area of concern for that organism, the score calculation director 204 may direct a calculation that uses the loci within the omic data pertaining to that particular area of concern. For instance, if demographic metadata suggests that prospective parents in a reproductive compatibility calculation are at an elevated risk for carrying a particular genetic disorder, the score calculation director 204 may direct a calculation that assesses the prospective parents' alleles at loci pertaining to that genetic disorder.

In some embodiments, score calculation director 204 may direct a calculation of the matching score without using secure, multiparty computation. In some embodiments, the omic data is conveyed from the second computing device 102a to the third computing device 102b via a secure channel protocol such as Secure Shell, instead of calculating the score using secure multiparty computation. For instance, where the matching score is a disease risk assessment score, the second computing device 102a is being operated by a user, and the third computing device 102b is being operated by an institution that intends to provide the user with the score, the user may direct the first computing device 102a to send the omic data containing the locus relevant to the disease in question to the third computing device 102b over a secure channel, and the third computing device 102b may calculate the disease risk assessment score using the transmitted omic data. In some embodiments, the second computing device 102a sends omic data directly to the first computing device 106a using an encrypted channel. In some embodiments, the first computing device 106a receives the omic data from the omic data provider 106b via a secure channel. In other embodiments, the matching score calculation is performed via a combination of secure multiparty computation and secure channel transmittal; for instance, each party's submission of secure shares to the secure multiparty computation may be transmitted over a secure channel.

In some embodiments, the first computing device 106a provides the matching score to at least one user. The first computing device 106a may provide the raw numerical score. The first computing device 106a may provide a qualitative description corresponding to the numerical score. For example, the first computing device 106a may provide a qualitative description that indicates, based on the quantity of the raw score, the likelihood of a disease. The qualitative description may describe the likely grade of a potential disease. The qualitative description may describe the likely severity of a potential disease. In some embodiments, the qualitative description indicates the severity of the overall numerical score; for instance, the qualitative description corresponding to a reproductive compatibility score may be taken from a range of descriptors from very low compatibility, indicating a high likelihood of a severe genetic disorder, to very high compatibility, indicating a very low likelihood of any genetic disorders. The first computing device 106a may match a numerical score to a qualitative description without determining the particular basis, in the omic data, for the numerical score; thus, the production of the qualitative score may not compromise the privacy of either set of omic data.

In some embodiments, the score calculation director 204 receives a score personalization instruction and directs the calculation of a matching score, by the second computing device and a third computing device, by means of a secure multiparty computation incorporating the score personalization instruction, using the at least one first input and at least one second input based upon a second set of omic data maintained by the third computing device. The score calculation director 204 may receive the score personalization instruction from the second computing device 102a. The score calculation director 204 may receive the score personalization instruction from the third computing device 102b. In some embodiments, the score calculation director 204 receives the score personalization instruction from a user via an additional computing device (not shown). In one embodiment, the score calculation director 204 receives a score personalization instruction emphasizing the significance of a particular finding. For instance, if the matching score is a reproductive compatibility score, one prospective parent may indicate that avoiding a particular genetic illness is especially important to that prospective parent. In another embodiment, the score calculation director 204 receives a score personalization instruction de-emphasizing the significance of a particular discovery. As an example, a prospective parent in a reproductive compatibility matching calculation may believe that treatment for a particular genetic condition has advanced to the point where the possibility of conceiving a child with that condition is not a concern. The score calculation director 204 may provide a user interface to the first computing device 102a or the second computing device 102b that lists potential discoveries of the omic matching calculation. The user interface may permit a user to rank potential discoveries relative to one another in order of importance to that user. The user interface may permit the user to ascribe absolute levels of importance to each listed potential discovery.

The score personalization instruction may specify one or more loci within the omic data to test in the matching score calculation. The score personalization instruction may specify one or more phenotypic attributes for which the matching score calculation should test. The score personalization instruction may specify one or more conditions for which the matching score calculation should test. For instance, where the calculation is to determine a disease risk assessment score, the calculation score director 204 may provide a user with a list of conditions based upon prevalence in the population. The user may add a condition that the user has reason to be concerned about, which was not previously on the list due to its rarity. The user may remove a condition from consideration as well. Each user's score personalization instructions may be visible to each other user who is a party to the matching score calculation. Alternatively, the score personalization instructions may be private, but the resulting list of loci and conditions to be assessed may be visible to each user.

In some embodiments, the score calculation director 204 modifies the score calculation to reflect the score personalization instructions. For instance, where the score personalization instruction adds a condition to be tested, the score calculation director 204 may obtain a secure calculation descriptor that includes the calculation to test for that condition. Where the score personalization instruction removes a phenotypic characteristic from consideration, the score calculation director 204 may obtain a secure calculation descriptor the does not include the calculation to test for that phenotypic characteristic. Where the score personalization instruction modifies the importance of a particular discovery, the calculation descriptor 204 may obtain a secure calculation descriptor that produces an output weighted according to the modified emphasis regarding that condition. The score calculation descriptor 204 may change the order in which it evaluates loci to prioritize loci corresponding to the most important phenotypic characteristics, as indicated by the score personalization instructions. In some embodiments, the first computing device 106a requests score personalization instructions prior to the first calculation of the matching score, to prevent a listener from deducing facts concerning the omic data from a change to the matching score due to the addition of the score personalization instruction. In some embodiments, the score personalization instruction specifies phenotypes to be verified; for instance, one party to a reproductive compatibility score calculation may wish to verify only certain desired traits, such as height or eye color, during the verification calculation. The verifier may modify the verification calculation in response to the score personalization request, by removing or adding calculations to be performed, or changing the order of the calculations, as described above.

In some embodiments, directing the calculation also includes: receiving from a second omic data provider a second set of verification data; requesting, by the first computing device and from the third computing device, a second verification output derived from the at least one second input; receiving, from the third computing device, the second verification output; and determining, by the first computing device, that the second verification output matches the second set of verification data. In some embodiments, the input verifier 202 receives verification data from the second omic data provider as described above for step 302. In some embodiments, the input verifier 202 requests the second verification output from the third computing device as set forth above for step 304. The input verifier 202 may receive the second verification output from the third computing device as described above in reference to step 306. The input verifier 202 may determine that the second verification output matches the second set of verification data as set forth above in reference to step 308. The input verifier 202 may obtain the second verification output via a secure multiparty computation as described above. The inputs of the third computing device 102b to the secure multiparty computation used to obtain the second verification output may be the same inputs the third computing device 102b uses for the matching score calculation. The secure shares that the third computing device 102b submits to the secure multiparty computation used to obtain the second verification output may be the same secure shares the third computing device 102b uses for the matching score calculation. The calculation descriptor used to obtain the second verification output may be integrated into a single calculation descriptor with the calculation descriptor used to calculate the matching score. The calculation descriptor used to obtain the second verification output may be further integrated with the verification calculation descriptor used to obtain the first verification output. The second computing device 102a may transmit the secure shares it receives from the third computing device 102b to the first computing device 106a so that the first computing device 106a can determine that the same inputs used to produce the second verification output are being used to calculate the matching score.

In some embodiments, the score calculation director 204 determines a subset of the first set of omic data, such that comparing the subset of the first set of omic data and a corresponding subset of the second set of omic data: reproduces the matching score; determines a biological description regarding the matching score using the subset of the first set of omic data; and transmits the biological description to the second computing device. The selection of the subset may be random. The selection of the subset may be a selection of some fraction of the total loci used in the initial matching score calculation, such as half of the total loci. The score calculation director 204 may select a subset of the loci by selecting one or more sets of loci associated with a particular discovery that could give rise to the matching score. For instance, if a reproductive compatibility score indicates a high probability of a serious genetic disorder, the score calculation director may include at least one locus associated with a serious genetic disorder in the subset.

In some embodiments, the score calculation director 204 discovers a subset of the omic data that produces the same matching score by: determining at least one trial subset of the first omic data; directing the calculation of a trial matching score, by the second computing device and the third computing device, by means of a secure function evaluation using the at least one trial subset and at least one corresponding subset of the second set of omic data; comparing, by the first computing device, the trial matching score to the matching score; and determining, by the first computing device, that the trial matching score is equal to the matching score. In some embodiments, the score calculation director 204 repeats that subdivision and recalculation process at least once to obtain a smaller subset of the first omic data. In one embodiment, the score calculation director 204 determines the precise set of loci within the omic data that gave rise to the matching score; for instance, in a reproductive compatibility score calculation, the matching score may indicate a high probability of a genetic disorder. In that case, the score calculation director 204 may find a subset of the genomic data consisting only of the loci that cause one particular genetic disorder.

In some embodiments, the score calculation director 204 determines a biological description corresponding to the subset of the first omic data. The score calculation director 204 may retrieve from memory accessible to the first computing device 106a a biological description corresponding to the subset; for example, a database table may contain records associating each set of loci that can give rise to a particular score with a biological description. In other embodiments, the score calculation director 204 may receive from the second computing device 102a the unencrypted omic data corresponding to the subset of the first omic data. The score calculation director 204 may use the unencrypted omic data to retrieve from memory accessible to the first computing device 106a a biological description corresponding to the unencrypted omic data. The biological description may describe a particular phenotypic attribute. The biological description may describe a particular disease. The biological description may describe a genetic disorder. The biological description may describe a reason why an organ donation may be rejected. In some embodiments, the first computing device 106a employs a protocol to determine the biological description while finding out the minimum necessary information concerning the first set of omic data and the second set of omic data; for instance, by discovering a subset of omic data that produces the matching score, the first computing device 106a may eliminate the need to discover any further information concerning the omic data not in the subset. Likewise, by using the locus pertaining to the matching score as the sole basis for determining the biological description, the first computing device 106a may furnish the description without discovering which set of omic data contains which bases for the matching score. For example, if one of two parties to a reproductive matching score has an allele at a particular locus that may give rise to a genetic disorder, the first computing device 106a may discover that the locus causes the reproductive compatibility score and describe the genetic disorder, without determining which party carries the allele in question.

In some embodiments, where a party to the matching score calculation has more than one distinct set of omic data relevant to the matching score, the first computing device 106a repeats the verification and matching score process at least once for each distinct set of omic data. For instance, when one party to the matching score calculation has more than one set of human genes, as in cases of chimerism or mosaicism, and the matching score calculation is one that depends on analysis of genetic data, the first computing device 106a may initiate a separate matching score and verification calculation for each distinct genome. For example, the first computing device 106a may initiate a separate reproductive compatibility score calculation for each possible combination of genomes presented by a pair of participants at least one of whom is chimeric; where both participants are chimeric, this may involve four separate reproductive compatibility score calculations, for instance.

In some embodiments, score calculation director 204 directs a secure multiparty computation that ranks a plurality of participants according to particular trait. For example, one participant to a reproductive compatibility score may enter a score personalization instruction indicating a list of phenotypic attributes desired or eschewed in a potential romantic partner, such as height or eye color. The participant may list genotypic attributes, such as presence or absence of known disease-causing alleles. The participant may list epigenetic attributes, such as epigenetic data indicating a history of substance abuse or of emotional trauma. The score calculation director 204 may perform a secure multiparty computation between multiple computing devices (not shown), each possessing one of the plurality of omic profiles. The secure multiparty computation may calculate a score for each omic profile of the plurality of omic profiles using the list of desired attributes. The secure multiparty computation may compare each omic profile to each other profile by combining a variation of the "millionaire's problem" protocol familiar to practitioners in the art with a sorting algorithm. The resulting ranking may arrange the other participants according to the listed preferences without revealing any of the attributes possessed by any one participant to any other participant or to the first computing device 106a. Likewise, the secure multiparty computation may not reveal to any of the ranked participants the criteria according to which they were ranked.

In some embodiments, the authenticator 206 authenticates at least one of the first set of omic data and the second set of omic data. The authenticator 206 may authenticate the first set of omic data. The authenticator 206 may authenticate the second set of omic data. The authenticator 206 may authenticate both the first set and the second set of omic data. In some embodiments, the authenticator 206 authenticates the omic data by determining that the omic data was provided by a trusted omic data provider. In some embodiments, the authenticator 206 authenticates the omic data by receiving, from at least one of the first omic data provider 106b or the second omic data provider 106c, metadata; providing, to a user, a security challenge; receiving, from the user, a response to the security challenge; and comparing the response to the metadata. The authenticator 206 may receive the metadata from the first omic data provider 106b. The authenticator 206 may receive the metadata from the second omic data provider 106c. The authenticator 206 may receive the metadata from both the first omic data provider 106b and the second omic data provider 106c. The security challenge may request the user to whom the omic data to be authenticated belongs to submit secret information. For instance, the security challenge may request that the user enter the date on which the user submitted the sample from which the omic data was derived.

In some embodiments, the authenticator 206 receives a response to the security challenge. The authenticator 206 may compare the response to the metadata. In some embodiments, the authenticator 206 determines whether the metadata precisely matches the response; for instance, if the security challenge asked for the date and time on which the sample was delivered by the user, the authenticator 206 may authenticate only if the user enters the correct date and time. In other embodiments, the authenticator 206 authenticates the omic data if the user enters an approximately correct response; for example, if the challenge question calls for a date and time, a response indicating the correct date and a time that is within a certain number of hours of the correct time may be sufficient.

The metadata may include phenotypic characteristics of the user, and the authenticator may receive at least one omic datum from the user, analyze the at least one omic datum for probable phenotypic characteristics, and compare the probable phenotypic characteristics to the phenotypic characteristics included in the metadata. For instance, the metadata may describe the eye color of the user. The security challenge may call for the portion of the user's genome that determines eye color, and the authenticator 206 may determine the probable eye color of the user, as predicted by the genome, and compare that probable eye color to the eye color described in the metadata. The omic data used for authentication may be a strictly limited subset of the overall omic data to be authenticated; as the verification process described above matches any portion of the omic data to the set of omic data as a whole, authentication of any subset of the omic data may authenticate the entire set. As a result, the first computing device 106a may learn only a minimal amount of additional information concerning the omic data set as a whole; for instance, the first computing device 106a may be able to determine the eye color of a person possessing the omic data set, while discovering nothing about potentially more sensitive issues such as disease risks or reproductive hazards. In some embodiments, the authenticator shares the calculation of the phenotypic attributes with an additional user; for instance, where the score to be calculated is a reproductive compatibility score, phenotypic information derived from the omic data of a first user may be conveyed to a second user to allow the second user to compare the phenotypic data to the physical appearance of the second user. Likewise, prior to a medical procedure, a medical worker may use the phenotypic information to visually confirm that the omic data likely matches a patient.

In some embodiments, the authenticator 206 receives, from at least one of the first omic data provider and the second omic data provider, mitochondrial data associated with the omic profile to be authenticated. The authenticator 206 may request, from a user, mitochondrial data. The authenticator 206 may receive, from the user, mitochondrial data. In some embodiments, the authenticator 206 authenticates the omic data by comparing the mitochondrial data received from the omic data provider to the mitochondrial data received from the user. The user of mitochondrial omic data may also enable the authenticator 206 to authenticate the omic data without discovering any information concerning the omic data besides that pertaining to mitochondria.

In some embodiments, the data used for authentication is encrypted by the omic data provider 106b prior to its transmittal to the first computing device. The data used for authentication may be divided into blocks and encrypted as described above for the creation of verification data in reference to FIG. 3. In some embodiments, the data used for authentication is part of the verification data. In some embodiments, the response to the challenge question is provided to the first computing device 106a by at least one of the second computing device 102a and the third computing device 102b, according to the processes described above in reference to FIG. 3 for provision of verification output to the first computing device 106a. As a result, the first computing device 106a may compare the authentication data to the response to the challenge question without possessing any unencrypted authentication data or challenge question responses. In some embodiments, the comparison of authentication data to challenge question responses is itself performed via a secure multiparty computation the output of which indicates only either that the authentication matches or does not match the challenge question response.

In some embodiments, one or more users initiate the above-described calculations by submitting a request to the first computing device 106a to initiate the calculation. The request may be entered via a website. The request may be entered via a mobile application. In some embodiments, a mobile application on a device used by one user detects the proximity of a device used by another user, and automatically requests a reproductive compatibility calculation involving the first user and the second user. In some embodiments, the detection is performed by an "always-on" application. The proximity-based initiation may occur by means of peer-to-peer communication between the two participants' computing devices; for instance, one participant's smartphone may detect the other participant's smartphone via a peer-to-peer communication technology such as near-field communication chips. In other embodiments, the proximity-based initiation occurs with the assistance of a remote device; as an example, two mobile devices may place one another within a particular geographical area by accessing the global positioning system. The matching score calculation may be initiated by detection of one computing device that the user of that computing device and the user of another computing device have enrolled in a common interaction, such as a class. The matching score calculation may be initiated by detection by one computing device that the user of that computing device and the user of another computing device are connected by a social networking platform, such as FACEBOOK. The common social interaction may involve attendance at a particular event. The common social interaction may involve attendance at a particular institution. In some embodiments, a reproductive compatibility match is initiated by a broader dating compatibility algorithm; for instance, a person who enters a profile on a dating website indicating the person's preferences in a romantic partner may initiate an automated search for a suitable partner by the website, which may include the initiation of a reproductive compatibility calculation. In some embodiments, the matching score calculation is used to anonymously determine a community of persons with a similar phenotypic attribute, allowing them to interact with each other while retaining as much privacy as they desire; for instance, the matching score may find a group of people likely to suffer from a particular genetic disease, so that they can support or advocate for each other. In some embodiments, the user swears under oath to the accuracy of the user's submitted omic data. In some embodiments, swearing under oath takes place instead of verification. In other embodiments, phenotypic data derived from the omic data is used to create a list of physical attributes or a pictorial rendition incorporating those attributes; the list or pictorial representation may be published in conjunction with the user's own description or photograph. The pictorial rendition or description may also describe the likely appearance of the children of prospective parents.

Figure 4:
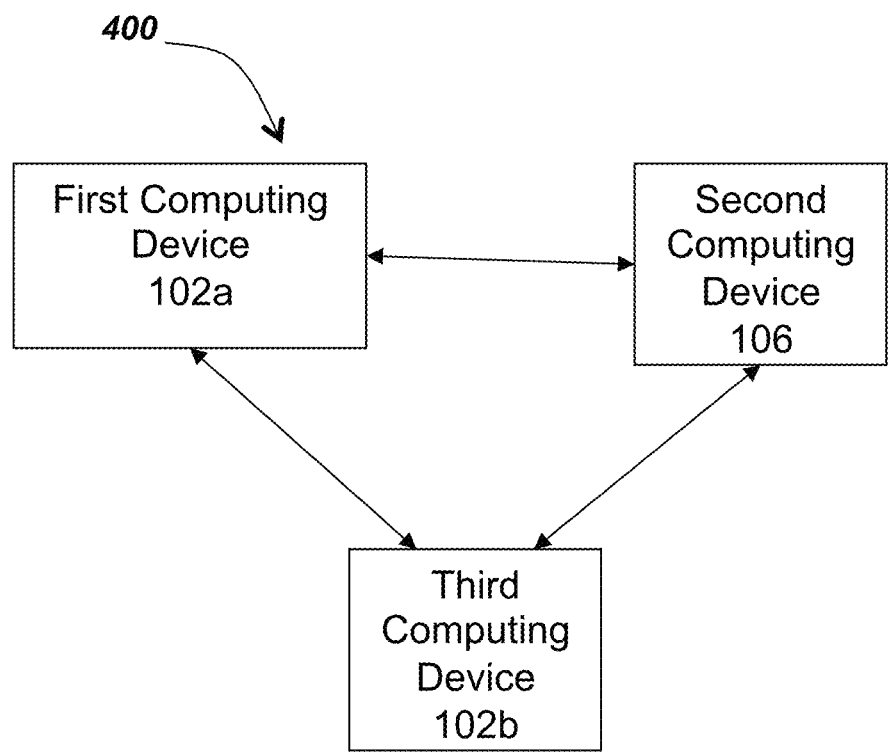
FIG. 4 is a schematic diagram depicting one embodiment of the disclosed system.

Referring now to FIG. 4, a schematic diagram depicts one embodiment of a system 400 for verifiable, private, and secure omic matching. The system 400 includes a first computing device 102a. In some embodiments, the first computing device 102a is a computing device 102 as described above in reference to FIGS. 1A-1C. In some embodiments the first computing device 102a is a computing device 106 as described above in reference to FIGS. 1A-1C. Also included in the system 400 is a second computing device 106, in communication with the first computing device 102a. The second computing device 106 may be a computing device 106 as described above in reference to FIGS. 1A-1C. The second computing device 106 may be a computing device 102 as described above in reference to FIGS. 1A-1C. The system 400 also includes a third computing device 102b. The third computing device 102b may be a computing device 102 as set forth above in reference to FIGS. 1A-1C. The third computing device 102b may be a computing device 106 as described above in reference to FIGS. 1A-1C.

Figure 5:
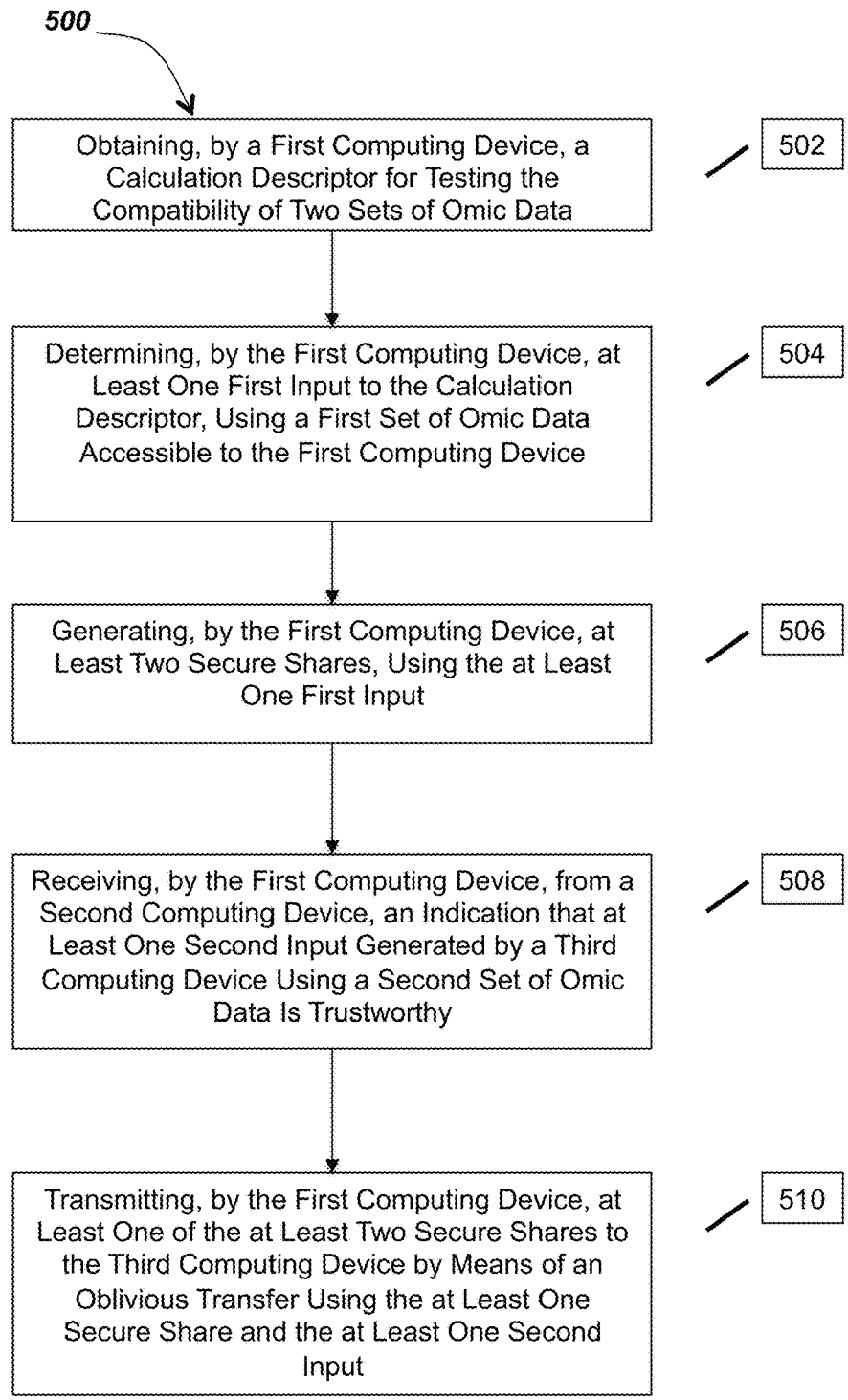
FIG. 5 is a flow diagram depicting an embodiment of a method for verifiable, private, and secure omic matching.

Referring now to FIG. 5, a flow diagram depicts one embodiment of a method for verifiable, private, and secure omic matching. In brief overview, the method 500 includes obtaining, by a first computing device, a calculation descriptor for testing the compatibility of two sets of omic data (502). The method 500 includes determining, by the first computing device, at least one first input to the calculation descriptor, using a first set of omic data accessible to the first computing device (504). The method 500 includes generating, by the first computing device, at least two secure shares, using the at least one first input (506). The method 500 includes receiving, by the first computing device, from a second computing device, an indication that at least one second input generated by a third computing device using a second set of omic data is trustworthy (508). The method 500 includes transmitting, by the first computing device, at least one of the at least two secure shares to the third computing device by means of an oblivious transfer using the at least one secure share and the at least one second input (510).

Reviewing FIG. 5 in more detail, and by reference to FIGS. 2A-2C, the method 500 includes obtaining, by a first computing device, a calculation descriptor for testing the compatibility of two sets of omic data (502). In some embodiments, the first computing device 102a generates a calculation descriptor as described above in reference to FIGS. 2A-2C. In other embodiments, the first computing device receives the calculation descriptor from the third computing device 102b. In some embodiments, the first computing device receives the calculation descriptor from the second computing device 106.

The first computing device 102a determines at least one first input to the calculation descriptor, using a first set of omic data accessible to the first computing device (504). In some embodiments, the first computing device 102a determines the input as described above in reference to FIG. 3.

The first computing device 102a generates at least two secure shares, using the at least one first input (506). In some embodiments, the first computing device 102a generates the at least two shares as described above in reference to FIGS. 2A-3.

The first computing device 102a receives from a second computing device 106, an indication that at least one second input generated by the third computing device using a second set of omic data is trustworthy (508). The second computing device 106 may determine that the at least one second input is trustworthy as described above for verification calculations in reference to FIG. 3.

The first computing device 102a transmits at least one of the at least two secure shares to the third computing device by means of an oblivious transfer using the at least one secure share and the at least one second input (510). In some embodiments, the oblivious transfer is performed as described above in reference to FIGS. 2A-3. In some embodiments, the first computing device receives at least one output generated using the at least one secure share, the at least one second input, and the calculation descriptor.

Figure 6:
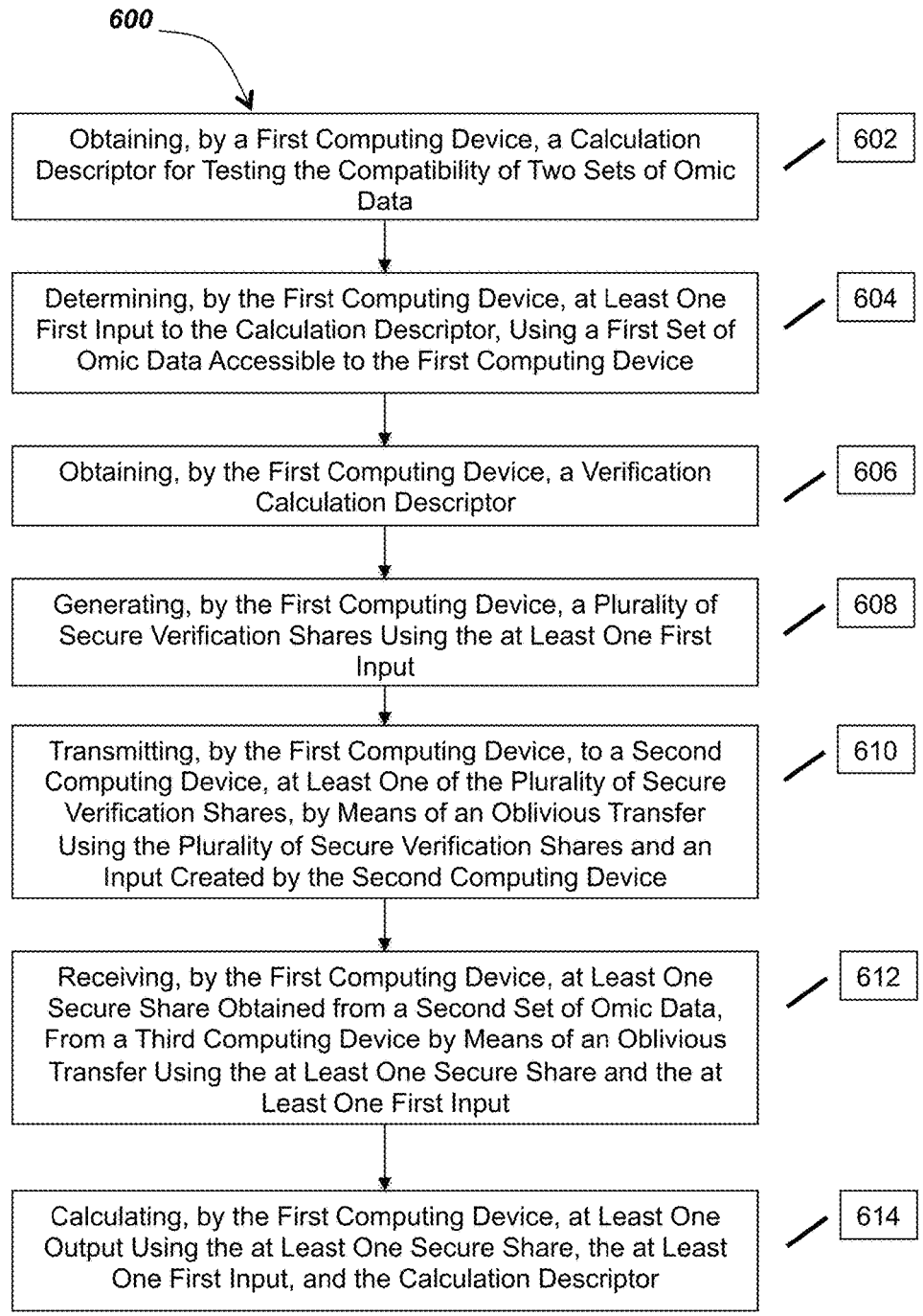
FIG. 6 is a flow diagram depicting an embodiment of a method for verifiable, private, and secure omic matching.

Referring now to FIG. 6, a flow diagram depicts one embodiment of a method 600 for verifiable, private, and secure omic matching. In brief overview, the method 600 includes obtaining, by a first computing device, a calculation descriptor for testing the compatibility of two sets of omic data (602). The method 600 includes determining, by the first computing device, at least one first input to the calculation descriptor, using a first set of omic data accessible to the first computing device (604). The method 600 includes obtaining, by the first computing device, a verification calculation descriptor (606). The method 600 includes generating, by the first computing device, a plurality of secure verification shares using the at least one first input (608). The method 600 includes transmitting, by the first computing device, to a second computing device, at least one of the plurality of secure verification shares, by means of an oblivious transfer using the plurality of secure verification shares and an input created by the second computing device (610). The method 600 includes receiving, by the first computing device, at least one secure share obtained from a second set of omic data, from a third computing device by means of an oblivious transfer using the at least one secure share and the at least one first input (612). The method 600 includes calculating, by the first computing device, at least one output using the at least one secure share, the at least one first input, and the calculation descriptor (614).

Reviewing FIG. 6 in more detail, and by reference to FIGS. 2A-2C, the method 600 includes obtaining, by a first computing device, a calculation descriptor for testing the compatibility of two sets of omic data (602). In some embodiments, the first computing device 102a generates a calculation descriptor as described above in reference to FIGS. 2A-3. In other embodiments, the first computing device 102a obtains the calculation descriptor by receiving the calculation descriptor from the third computing device 102b. In other embodiments, the first computing device 102a obtains the calculation descriptor by receiving a calculation descriptor from the second device 106.

The first computing device determines at least one first input to the calculation descriptor, using a first set of omic data accessible to the first computing device (604). In some embodiments, the first computing device determines the at least one first input as described above in reference to FIGS. 2A-3.

The first computing device 102a obtains a verification calculation descriptor (606). In one embodiment, the first computing device 102a generates the calculation descriptor as described above in reference to FIGS. 2A-3. In another embodiment, the first computing device 102a obtains the verification calculation descriptor from the third computing device 102b. In still another embodiment, the first computing device 102a obtains the verification calculation descriptor by receiving the verification calculation descriptor from the second computing device 106.

The first computing device generates at least two secure verification shares using the at least one first input (608). In some embodiments, the first computing device generates the at least two verification shares according to secure share generation processes as described above in reference to FIGS. 2A-3.

The first computing device 102a transmits at least one of the plurality of secure verification shares to a second computing device 106 by means of an oblivious transfer using the plurality of secure verification shares and an input created by the second computing device (610). In some embodiments, the first computing device 102a and the second computing device 106 perform the oblivious transfer as described above in reference to FIGS. 2A-3.

The first computing device 102a receives at least one secure share obtained from a second set of omic data from a third computing device 102b by means of an oblivious transfer using the at least one secure share and the at least one first input (612). In some embodiments, the first computing device 102a and the third computing device 102b perform the oblivious transfer as described above in reference to FIGS. 2A-3.

The first computing device calculates at least one output using the at least one secure share, the at least one first input, and the calculation descriptor (614). In some embodiments, the first computing device 102a calculations the at least one output as described above in reference to FIG. 3.

Figure 7A:
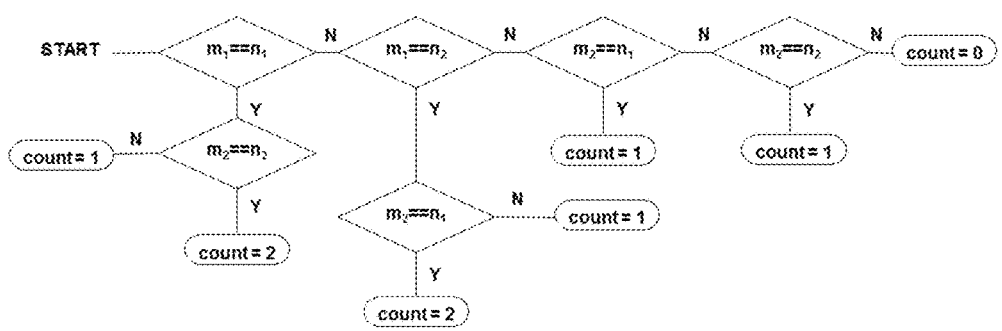
FIG. 7A is a flow diagram depicting an exemplary process for transfusion donor and recipient matching.
Figure 7B:
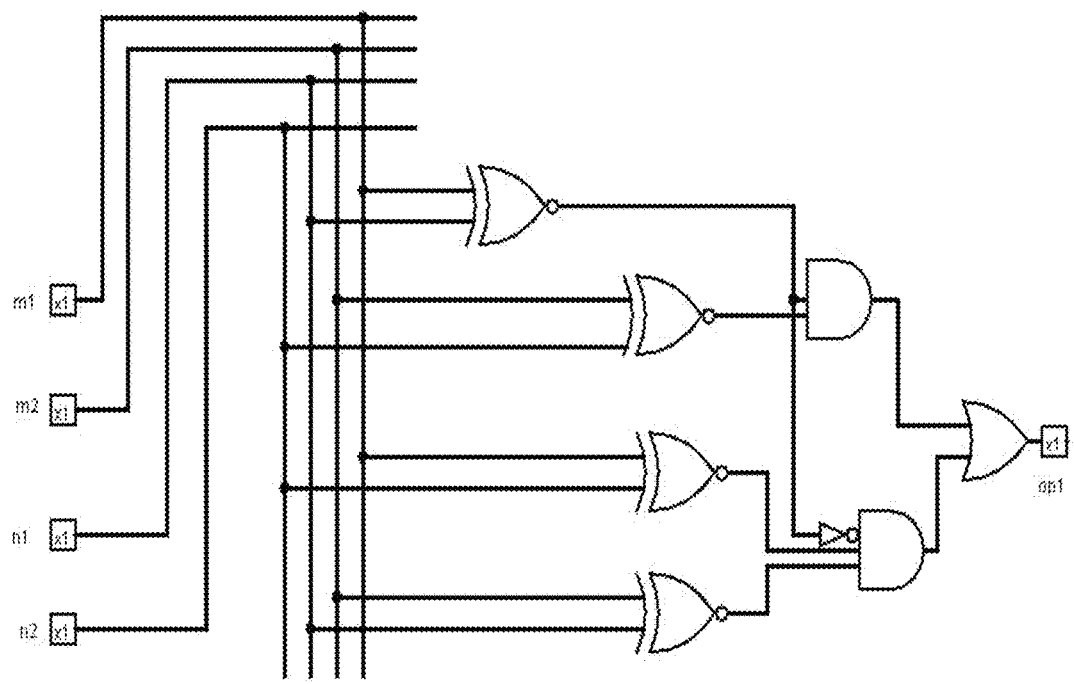
FIG. 7B is a schematic diagram depicting a Boolean circuit for transfusion donor and recipient matching.
Figure 7C:
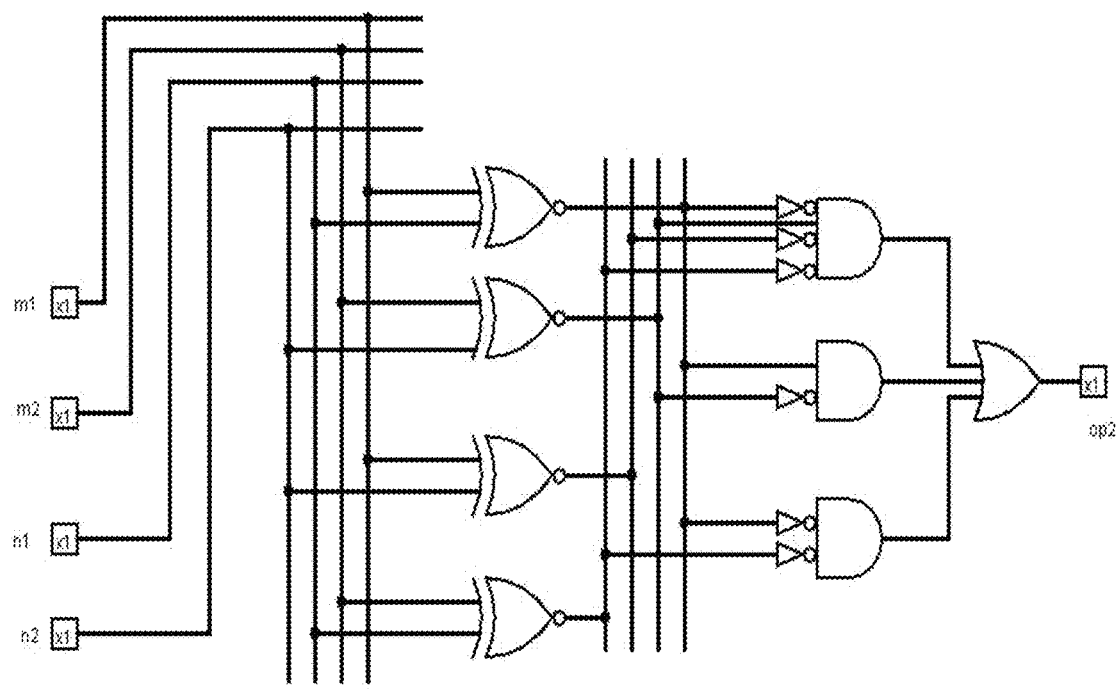
FIG. 7C is a schematic diagram depicting a Boolean circuit for transfusion donor and recipient matching.

FIGS. 7A-7C illustrate one of example of a calculation to determine the suitability of a donor for a transfusion, by screening for human leukocyte antigen ("HLA") types, to determine whether a donor and donee are a suitable match, and the extent to which their match is suitable. In the example, the donee, Alice, wishes to know whether the ten alleles corresponding to the HLA-A, HLA-B, HLA-C, HLA-DRB1, and HLA-DQB1 genes of the donor, Bob, match the corresponding ten alleles in Alice's genes, at the protein coding level. Continuing the example, the circuit for the HLA-A gene may be constructed as follows: if the two HLA-A alleles for Alice and Bob are represented by $\{m_1, m_2\}$ for Alice, and $\{n_1, n_2\}$ for Bob, the flowchart indicating the decision process to be represented by a Boolean circuit is shown in FIG. 7A; representing those inputs in binary form by setting m1=0, m2=1, n1=0, and n2=1, and representing the extent to which the alleles match with a two bit output count 0=00, 1=01, 2=10, where 0 is the best possible match and 2 is the worst possible match, FIG. 7B depicts a Boolean circuit for the first output bit, and FIG. 7C depicts a Boolean circuit for the second output bit, using the same representational conventions used above in reference to FIGS. 2B and 2C. In the same example similar circuits may be constructed for each of the four other genes.

Similarly, in an example where Alice wants to know if there are any users in a database listing individuals' HLA types with whom she shares at least k alleles, evaluation of a set of similar circuits to those in 7B and 7C may return the count of matching alleles in {0,1,2} for the gene under consideration; Alice's genes may be matched against all the users in the database in a pairwise fashion and all users where the count >=k will be returned. In yet another example, the same protocol may select suitable donors from a community of users available to perform a matching score calculation by virtue of being 'online' through the agency of an application or software client installed on their computing devices; in some embodiments, a remote device such as a remote device 106a described above in reference to FIGS. 2A-3 may coordinate the selection of a user population to participate in the selection protocol. Skilled practitioners in the art will recognize that a similar matching protocol may also be performed regarding other polymorphic loci apart from the Type I (HLA-A, HLA-B, HLA-C) genes such as Type II genes, MICA, MICB, TAP1, TAP2, and the KIR locus. Other matching protocols may involve HLA haplotype matching, which is matching of sets of two or more alleles deriving from the same chromosome. Additional calculations screening for other phenotypic characteristics such as age, ethnicity, and gender may also be included in the matching score calculation, as described above in reference to FIGS. 2A-3.

Figure 8:
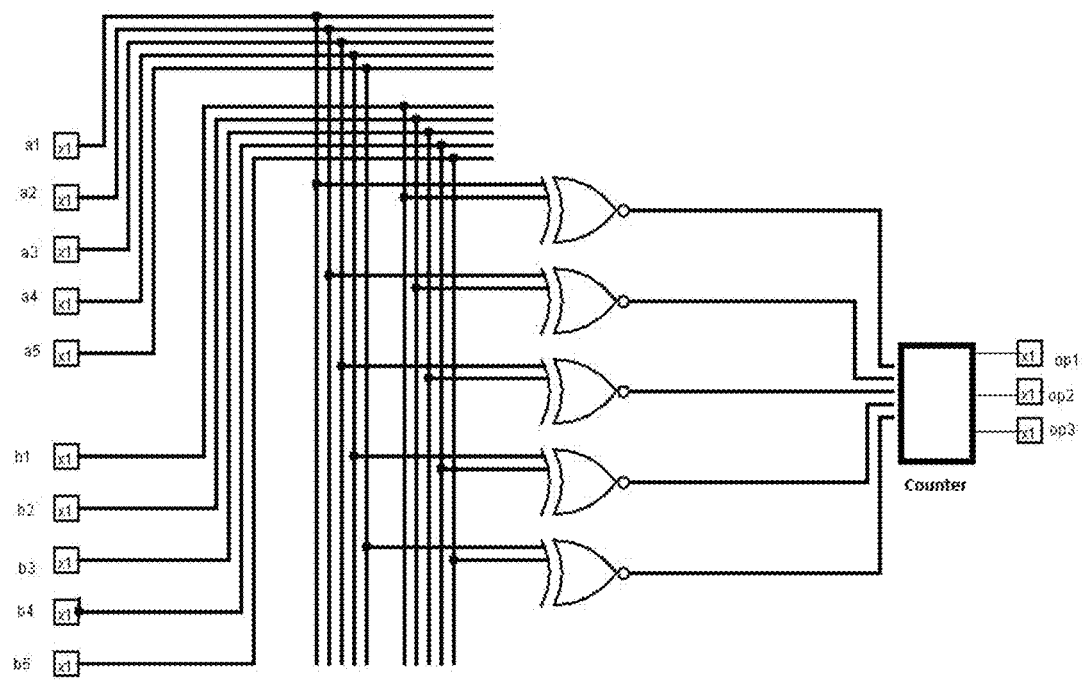
FIG. 8 is a schematic diagram depicting a Boolean circuit for relatedness estimation.

FIG. 8 illustrates an exemplary matching score calculation to determine how related two individuals are, by means of most recent common ancestor (MRCA) determination. In this example, Adam and Bob each possesses the non-recombining portion of his Y chromosome, evaluated at n positions, and match at k of the n loci; assuming an Infinite Alleles Model (IAM) and a flat prior, and given mutation rate p and time period in generations to the most common ancestor t, the posterior distribution of the time to MRCA in generations p(t) may be determined by the following equation:

$$p(t) = \left( \frac{\prod_{i=0}^{n-k} [2\mu(n-i)]}{2^{n-k}(n-k)!\mu^{n-k}} \right) \frac{(1-e^{-2\mu t})^{n-k}}{e^{2\mu k t}}$$

Continuing the example, the mean and variance of the posterior distribution may be calculated for particular values of the parameters, and the mean or the mode (maximum likelihood estimate) of the posterior distribution may be used as an estimate of t; estimates of t and its associated variance for different parameter values may also be precomputed and stored in a lookup table. As a further illustration of the same example, where Adam and Bob have been genotyped at 5 positions and their respective values at the 5 positions are {$a_1, a_2, a_3, a_4, a_5$} and {$b_1, b_2, b_3, b_4, b_5$} respectively, the relevant portion of a lookup table listing estimates of t with standard variations may appear as follows:

| n | k | t | standard deviation |
|---|---|---|---|
| 5 | 5 | T1 | s(T1) |
| 5 | 4 | T2 | s(T2) |
| 5 | 3 | T3 | s(T3) |
| 5 | 2 | T4 | s(T4) |
| 5 | 1 | T5 | s(T5) |
| 5 | 0 | T6 | s(T6) |

Continuing the example, the circuit may first calculate k by comparing ($a_i, b_i$) pairs and then look up the above table and fetch the appropriate value for t and its associated standard deviation, and then use a counter to output the number of matches k; in this case (n=5), the output is 3 bits long. FIG. 8 depicts one embodiment of a circuit performing the calculation in the above example. In other embodiments, the circuit may incorporate mutation rates differing from the Infinite Alleles Model, such as the Stepwise Mutation Model. Still other embodiments may use microsatellite information involving which higher mutation rates. Persons skilled in the art will be aware that other embodiments, may incorporate both SNP and microsatellite data (for example on the Y chromosome). Other approaches that utilize autosomal or recombining regions of the genome may also be utilized.

Another exemplary use of the above system and method involves the annotation of omic data. As a non-limiting example, where the omic data is the genome of a person, stored as a set of differences from a representative genome as described above in reference to FIG. 2A, and available as a table of polymorphisms consisting of SNPs and indels, either directly generated or derived from a bam file containing all reads generated during the sequencing, the person uploads or submits her genotype for one or more matching scores as described above in reference to FIG. 2A. Continuing the example, the genotype is compared against a table of known polymorphisms whose impacts are known independently or in context, generating a list of risks and strengths can be generated, or an aggregated score. As a further illustration, a back-end table of known polymorphisms may look similar to this example table, where the health risk index may be calculated based on parameters such as mortality and health care costs:

| Chromosome | Position | Risk Allele | Known effect | Health risk index assigned |
|---|---|---|---|---|
| 2 | 24529 | A/G | Correlated strongly with condition 'b' | −0.7 |
| 3 | 560945 | T/T | Causes recessive disease X (late onset) | −0.5 |
| 5 | 131313 | A/N | Correlated with 'c'-degeneration | −0.3 |
| 7 | 200012 | C/T | Aggravates disease X leading to Y if Chr3-560945 is T/T | −0.2 |
| Y | 57001222 | G | non-lethal condition 'a' | −0.05 |

In a additional example Bob has submitted his genotype for analysis, and the following table has been generated:

| Chromosome | Position | Genotype | Effect | Bob's weightage | Score |
|---|---|---|---|---|---|
| 1 | 3000010 | AG | — | 1 | |
| 2 | 24529 | CC | — | 1 | 0 |
| 3 | 560945 | AG | — | 0.2 | 0 |
| 5 | 131313 | CT | 'c' degeneration | 0.5 | −0.15 |
| 5 | 1315291 | TT | — | 1 | |
| 7 | 200012 | CC | — | 1 | 0 |
| 11 | 14299121 | TA | — | 1 | |
| 13 | 98453 | AA | — | 0.75 | |
| 17 | 119982 | CC | — | 1 | |
| Y | 57001222 | T | — | 1 | 0 |

In this example, out of Bob's submitted genotype, only the rows corresponding to known effects, such as rows chr2-24529, chr3-560945, chr5-131313, chr7-200012 and Y-57001222, are considered in calculating the aggregate score. Continuing the example, the aggregate score is the sum of weighted scores for all loci where weighted score is weightage*health index. Further continuing the example, the aggregate score is −0.15, and may be summarized by stating that Bob has a risk of 'c' degeneration; a detailed description may inform Bob that Bob has a risk of 'c' degeneration due to the presence of CT alleles at 131313 on chromosome 5, but that although Bob has CC alleles at 200012 on chromosome 7, it is not an indication for a possibility of disease Y because Bob does not have the primary causative alleles at 560945 on chromosome 5. Practitioners skilled in the art will be aware that Bob's submitted genotype is may represent quite a large dataset compared to known polymorphisms table for years to come, resulting in a more complex computation for the aggregate score. In other embodiments, Bob's data may include copy number variants (CNVs), methylation status and other genomic features, or the entire genome with various epigenetic modifications specified. In still other embodiments, the omic data may be any omic data described above in reference to FIG. 2A, including the person's genome, transcriptome, microbiome, or metabolome. The output of the annotation process may be displayed to the person or persons whose omic data is annotated. In other embodiments omic annotation of a humorous or entertaining nature may be published to a website or social network.

Embodiments of the above-described system and method permit users to discover medical issues latent in their omic profiles without fear of stigma due to privacy breaches. A person who has a particular concern with regard to his or her omic profile may tailor the calculation to address that concern. In some embodiments, the use of secure multiparty calculation to discover the matching score ensures that neither party to the calculation discovers the omic data of the other party; the secure multiparty calculation also protects the privacy of the omic data from third-party listeners, including an authentication server. The use of secure multiparty computation and homomorphic encryption to verify omic data may enable the authentication server to guarantee both that the omic data is genuine and that the authentication server retains no unencrypted version of the omic data, limiting fears of security breaches and data mining. Safeguards against malicious users help to ensure the privacy and authenticity of the calculations.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C#, JAVA, or any compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices; firmware; programmable logic; hardware (e.g., integrated circuit chip, electronic devices, a computer-readable non-volatile storage unit, non-volatile memory, such as semiconductor memory devices, including EPROM, EEPROM, and flash memory devices); magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data from a second computer providing access to the programs via a network transmission line, wireless transmission media, signals propagating through space, radio waves, infrared signals, etc.

Having described certain embodiments of methods and systems for verifiable, private, and secure omic matching, it will now become apparent to one of skill in the art that other embodiments incorporating the concepts of the disclosure may be used. For example, while certain system infrastructure elements are illustrated in particular configurations, it is understood and contemplated that functional elements described herein can be readily integrated and/or implemented via various alternative hardware or software implementations, as would be known to a person of skill in the field of information systems design.

Moreover, while certain embodiments of the invention have been described herein in detail for purposes of clarity and understanding, the foregoing description and Figures merely explain and illustrate the present invention and the present invention is not limited thereto. It will be appreciated that those skilled in the art, having the present disclosure before them, will be able to make modifications and variations to that disclosed herein without departing from the scope of any appended claims.

The invention claimed is:

1. An omic compatibility matching system implemented on a host computing device communicating with a first user computing device storing a first set of omic data associated with a first user, and with a second user computing device storing a second set of omic data associated with a second user, the computing devices communicating via a digital communications network to execute an omic matching transaction with authenticated data provenance, the computing devices each having one or more processors and memory storing instructions which, when executed by the processors, cause the computing devices to perform a method comprising:

generating, by the host computing device, a calculation descriptor for testing the compatibility of the first set of omic data and the second set of omic data;

generating, by the host computing device, verification data for the first set of omic data;

generating a verification calculation descriptor for the first set of omic data, for verifying through a secure computation that the inputs provided to the calculation descriptor are the same as the inputs previously presented to the host device and associated with the first user;

transmitting the verification calculation descriptor to the first user computing device;

transmitting the calculation descriptor to the second user computing device;

calculating, by the host computing device and the first user computing device, a verification output using the verification calculation descriptor and the first set of omic data, the verification output indicating whether the first set of omic data is the same as omic data previously presented to the host device by the first user;

transmitting, by the first user computing device to the host computing device and the second user computing device, an input to the calculation descriptor;

reporting to the host computing device, by the second user computing device, the input to the calculation descriptor received from the first user computing device; and determining, by the host computing device, that the input to the calculation descriptor provided to the host computing device by the first user computing device is the same as the input reported by the second user computing device and that the verification calculation descriptor has verified that the inputs provided to the calculation descriptor are the same as the inputs previously presented to the host device and associated with the first user, and only then, substantially simultaneously directing, by the host computing device, the calculation of a compatibility score by the first user computing device and the second user computing device using a secure function evaluation based on the calculation descriptor, the first set of omic data, and the second set of omic data.

2. A method for omic compatibility matching with authenticated data provenance by a first user computing device storing a first set of omic data that is associated with a first user, communicating via a digital communications network with a second user computing device storing a second set of omic data that is associated with a second user, and a host computing device, without revealing any user's omic data to a computing device other than the device on which the omic data is stored, the method comprising:

receiving, by the first user computing device, a calculation descriptor for testing the compatibility of the first set of omic data with the second set of omic data;

determining, by the first user computing device, at least one first input to the calculation descriptor, using the first set of omic data;

generating, by the first user computing device, at least one secure share, using the at least one first input;

receiving, by the first user computing device, from the host computing device, an indication that at least one second input generated by the second user computing device using the second set of omic data is trustworthy based on application of a verification calculation descriptor to at least one calculation descriptor input provided to the host computing device from the second user computing device to verify that the second input is the same as input data previously presented to the host computing device by the second user, and only then, substantially simultaneously transmitting, by the first user computing device, the at least one secure share to the second user computing device by means of an oblivious transfer using the at least one secure share and the at least one second input; and receiving, from the second computing device, by the first user computing device, at least one output indicative of omic compatibility between the first set of omic data and the second set of omic data, the at least one output generated using the at least one secure share, the at least one second input, and the calculation descriptor.

3. The method of claim 2, wherein the calculation descriptor is received from the host computing device, the calculation descriptor also being shared by the host computing device with the second user computing device.

4. The method of claim 2, wherein the calculation descriptor comprises a boolean circuit comprising a set of logically interrelated gates.

5. The method of claim 2, further comprising:

determining, by the first user computing device, a subset of the first set of omic data, such that comparing the subset of the first set of omic data and a corresponding subset of the second set of omic data reproduces the at least one output;

transmitting, by the first user computing device, the subset of the first set of omic data to the host computing device; and receiving, by the first user computing device and from the host computing device, a biological description regarding the at least one output, using the subset of the first set of omic data and the subset of the second omic data.

6. The method of claim 5, wherein the step of determining, by the first user computing device, a subset of the first set of omic data, further comprises the substeps of:

dividing the first set of omic data to obtain the subset of the first set of omic data;

obtaining, by the first user computing device, an additional calculation descriptor for comparing the subset of the first set of omic data with the analogous subset of the second set of omic data;

determining, by the first user computing device, at least one additional input to the calculation descriptor, using the subset of the first set of omic data;

generating, by the first user computing device, at least one additional secure share, using the at least one additional input;

transmitting, by the first user computing device, the at least one additional secure share to the second user computing device by means of an oblivious transfer using the at least one additional secure share and an additional second input from the second user computing device;

receiving, by the first user computing device, at least one additional output generated using the at least one secure share, the at least one second input, and the calculation descriptor;

comparing, by the first user computing device, the at least one additional output to the at least one output; and determining, by the first user computing device, that the at least one additional output is equal to the at least one output.

7. A method for omic compatibility matching with authenticated data provenance by a first user computing device storing a first set of omic data that is associated with a first user, communicating via a digital communications network with a second user computing device storing a second set of omic data that is associated with a second user, and a host computing device, without revealing any user's omic data to a computing device other than the device on which the omic data is stored, the method comprising:

generating, by the host computing device, a calculation descriptor for testing the compatibility of the first set of omic data and the second set of omic data;

generating a verification calculation descriptor for the first set of omic data, the verification calculation descriptor verifying, through a secure computation, that the inputs provided to the calculation descriptor are the same as the inputs previously presented to the host computing device and associated with the first user;

generating, by the host computing device, verification data for the second set of omic data;

receiving, by the first user computing device, a calculation descriptor for testing the compatibility of the first set of omic data and the second set of omic data;

determining, by the first user computing device, at least one first input to the calculation descriptor, using the first set of omic data;

committing, by the first user computing device, to the at least one first input;

obtaining, by the first user computing device, the verification calculation descriptor;

generating, by the first user computing device, a secure verification share by applying the verification calculation descriptor to the at least one first input;

transmitting, by the first user computing device, to a host computing device, the secure verification share, by means of an oblivious transfer using the at least one secure verification share and an input created by the host computing device;

receiving, by the first user computing device, at least one secure share obtained from the second set of omic data, from the second user computing device by means of an oblivious transfer using the at least one secure share and the at least one first input; and calculating, by the first user computing device, at least one output indicative of omic compatibility between the first set of omic data and the second set of omic data, the at least one output calculated using the at least one secure share, the at least one first input, and the calculation descriptor.

8. The method of claim 7, wherein the calculation descriptor is a boolean circuit comprising a set of logically interrelated gates, and having a first set of input wires corresponding to the first set of omic data, and a second set of input wires corresponding to the second set of omic data.

9. The method of claim 8, wherein calculating at least one output further comprises calculating at least one output using a Gate Evaluation Secret Sharing scheme.

10. A method for a plurality of user computing devices to evaluate omic compatibility amongst a plurality of sets of omic data, each set of omic data stored on a different user computing device, without revealing any one set of omic data to a user computing device storing any other set of omic data, the method comprising:

selecting, by a user computing device, a set of comparison attributes from amongst a plurality of omic attributes for comparing the sets of omic data;

for each user computing device, obtaining user preferences associated with the user of the computing device;

determining, by each user computing device, user-specific weighting factors for the attributes based on the user preferences;

verifying, using a verification calculation descriptor that employs a secure computation, that at least a first set of omic data, from amongst the plurality of sets of omic data used in the calculation, is the same as omic data previously presented to a host device for association with the first user;

computing a numerical subscore for each attribute by comparing the sets of omic data based upon the selected set of comparison attributes using a secure multiparty computation;

applying, by each user computing device, the user-specific weighting factors to the numerical subscores for each attribute to generate custom-weighted subscores for each user; and calculating, by each user computing device, a personalized matching score by combining the custom-weighted subscores for each user.

11. The method of claim 10, in which the personalized matching score is a reproductive compatibility score indicative of reproductive compatibility between two users.

12. The method of claim 10, in which the plurality of sets of omic data comprise: an omic data set of associated with a biological organism; and one or more data sets associated with a probability of developing one or more illnesses;

and in which the personalized matching score is a disease risk assessment score evaluating risk of the biological organism developing the one or more illnesses.

13. The method of claim 10, in which at least one of the plurality of sets of omic data is associated with a potential organ donee, and at least one of the plurality of sets of omic data is associated with an organ donor; and in which the matching score is an organ donation compatibility score.

14. The method of claim 10, in which the plurality of sets of omic data comprise a first set of omic data associated with a first biological organism, and a second set of omic data associated with a second biological organism; and in which the matching score is a relatedness score, determining relatedness between the first and second biological organisms.

15. The method of claim 10, in which the comparison attributes comprise one or more phenotypic attributes; and in which the user preferences comprise preferences for traits associated with said phenotypic attributes.

16. The method of claim 2, in which the first user computing device is a mobile phone, the second user computing device is a mobile phone, and the host computing device is a network-connected server.

17. The method of claim 7, in which the first user computing device is a mobile phone, the second user computing device is a mobile phone, and the host computing device is a network-connected server.

* * * * *